(12) United States Patent
Zheng et al.

(10) Patent No.: US 11,866,491 B2
(45) Date of Patent: Jan. 9, 2024

(54) ANTIBODY FOR BINDING TO INTERLEUKIN 4 RECEPTOR

(71) Applicant: SUZHOU CONNECT BIOPHARMACEUTICALS, LTD., Taicang (CN)

(72) Inventors: Wei Zheng, San Diego, CA (US); Wubin Pan, Richmond (CA); Xin Yang, Taicang (CN); Yang Chen, Taicang (CN); Limin Zhang, Taicang (CN); Jie Jiang, Taicang (CN)

(73) Assignee: SuZhou Connect Biopharmaceuticals, Inc., Taicang (CN)

( * ) Notice: Subject to any disclaimer, the term of this patent is extended or adjusted under 35 U.S.C. 154(b) by 603 days.

(21) Appl. No.: 16/994,464

(22) Filed: Aug. 14, 2020

(65) Prior Publication Data

US 2021/0079088 A1 Mar. 18, 2021

Related U.S. Application Data

(60) Division of application No. 16/809,411, filed on Mar. 4, 2020, now Pat. No. 10,774,141, which is a continuation-in-part of application No. 16/307,930, filed as application No. PCT/CN2017/087592 on Jun. 8, 2017, now abandoned.

(30) Foreign Application Priority Data

Jun. 8, 2016 (CN) .......................... 201610399254.4

(51) Int. Cl.
| | |
|---|---|
| *A61K 39/395* | (2006.01) |
| *C07K 16/24* | (2006.01) |
| *A61P 37/08* | (2006.01) |
| *A61P 29/00* | (2006.01) |
| *C07K 16/28* | (2006.01) |
| *C12N 5/12* | (2006.01) |
| *C12N 15/62* | (2006.01) |
| *C12N 15/85* | (2006.01) |
| *A61K 38/00* | (2006.01) |
| *A61K 45/06* | (2006.01) |

(52) U.S. Cl.
CPC .......... *C07K 16/247* (2013.01); *A61K 39/395* (2013.01); *A61P 29/00* (2018.01); *A61P 37/08* (2018.01); *C07K 16/28* (2013.01); *C12N 5/12* (2013.01); *C12N 15/62* (2013.01); *C12N 15/85* (2013.01); *A61K 38/00* (2013.01); *A61K 45/06* (2013.01); *C12N 2015/8518* (2013.01)

(58) Field of Classification Search
CPC ....... A61K 39/395; A61K 38/00; C07K 16/28
See application file for complete search history.

(56) References Cited

U.S. PATENT DOCUMENTS

| | | | |
|---|---|---|---|
| 7,638,606 B2 | 12/2009 | Carter et al. | |
| 8,679,487 B2 | 3/2014 | Armitage et al. | |
| 9,290,574 B2 | 3/2016 | Kostic et al. | |
| 9,334,331 B2 * | 5/2016 | Igawa | C07K 16/40 |
| 10,421,807 B2 * | 9/2019 | Gonzales | A61P 11/00 |
| 10,485,844 B2 | 11/2019 | Radin et al. | |
| 10,730,948 B2 | 8/2020 | Kostic et al. | |
| 10,774,141 B2 | 9/2020 | Zheng et al. | |
| 2016/0363591 A1 | 12/2016 | Streicher et al. | |
| 2018/0016343 A1 | 1/2018 | Ardeleanu et al. | |
| 2019/0040126 A1 | 2/2019 | Radin et al. | |
| 2019/0183973 A1 | 6/2019 | Hamilton et al. | |
| 2019/0345253 A1 | 11/2019 | Bansal | |
| 2019/0367622 A1 | 12/2019 | Graham et al. | |
| 2019/0367624 A1 | 12/2019 | Dix et al. | |
| 2020/0283518 A1 | 9/2020 | Liot et al. | |

FOREIGN PATENT DOCUMENTS

| | | |
|---|---|---|
| CN | 1886426 A | 12/2006 |
| CN | 101522716 A | 9/2009 |
| CN | 103998053 A | 8/2014 |
| CN | 108339118 A | 7/2018 |
| CN | 109789196 A | 5/2019 |
| CN | 111526920 A | 8/2020 |
| CN | 111686247 A | 9/2020 |
| CN | 111939261 A | 11/2020 |
| CN | 112153982 A | 12/2020 |
| EP | 2990420 B1 | 7/1992 |
| EP | 2292665 A1 | 3/2011 |
| EP | 2990420 B1 | 12/2016 |
| EP | 2892927 B1 | 5/2018 |
| EP | 3354663 A1 | 8/2018 |
| EP | 3470430 A1 | 4/2019 |
| WO | 01/92340 A2 | 12/2001 |
| WO | 2005/047325 A2 | 5/2005 |

(Continued)

OTHER PUBLICATIONS

Kau et al, Current Opinion Allergy Clinical Immunology, 2014, vol. 14. No. 6, pp. 570-575.*
Le Floch et al, (Allergy. 2020; vol. 75, pp. 188-1204).*
Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Poosarla et al. (2017, Biotechn. Bioeng. 114(6): 1331-1342).*
Rabia, et al. (2018, Biochemical Engineering Journal 137:365-374).*
Khan et al. (2014, J. Immunol. 192: 5398-5405).*
Brummell et al. (Biochemistry 32:1180-1187 (1993)).*
Kobayashi et al. (Protein Engineering 12:879-844 (1999)).*

(Continued)

*Primary Examiner* — Gyan Chandra
(74) *Attorney, Agent, or Firm* — Goodwin Procter LLP

(57) ABSTRACT

Disclosed is an antibody capable of binding to the interleukin 4 (IL-4) receptor (IL-4). Also disclosed are a nucleic acid sequence encoding the antibody, a vector including the nucleic acid sequence, and a host cell transformed or transfected with the vector. Provided are a method for producing the antibody, a medical use of the antibody, and a kit including the antibody.

32 Claims, 5 Drawing Sheets

Specification includes a Sequence Listing.

(56) References Cited

FOREIGN PATENT DOCUMENTS

| WO | 2005/047331 | A2 | 5/2005 |
|---|---|---|---|
| WO | 2008/054606 | A2 | 5/2008 |
| WO | 2009/121847 | A2 | 10/2009 |
| WO | 2010/070346 | A2 | 6/2010 |
| WO | 2012071372 | A2 | 5/2012 |
| WO | 2013/087660 | A1 | 6/2013 |
| WO | 2015/130975 | A1 | 9/2015 |
| WO | 2018/045130 | A1 | 3/2018 |
| WO | 2018/057776 | A1 | 3/2018 |
| WO | 2019/089473 | A1 | 5/2019 |
| WO | 2020/096381 | A1 | 5/2020 |
| WO | 2020/180727 | A1 | 9/2020 |
| WO | 2020/182197 | A1 | 9/2020 |

OTHER PUBLICATIONS

Coleman (Research in Immunol. 145:33-36 (1994)).*
Casset et al (Biochemical and Biophysical Research Communications, 307:198-205, 2003).*
Rudikoff, et al. (Proc. Natl. Acad. Sci. USA, 79(6):1979-1983, 1982).*
Burks et al. (PNAS 94:412-417 (1997)).*
Brorson et al. (J. Immunol. 163:6694-6701 (1999)).*
International Search Report dated Aug. 25, 2017 for corresponding PCT Application No. PCT/CN2017/087592 (10 pages).
Supplementary European Search Report for International Application No. EP17809758, dated Apr. 22, 2020, 22 pages.
Angal et al., A Single Amino Acid Substitution Abolishes the Heterogeneity of Chimeric Mouse/Human (IgG4) Antibody, Mol Immunol. 1993; 30:105-08.

* cited by examiner

ANTIBODY FOR BINDING TO INTERLEUKIN 4 RECEPTOR

CROSS-REFERENCE TO RELATED APPLICATIONS

The present application is a divisional of U.S. application Ser. No. 16/809,411, filed Mar. 4, 2020, now U.S. Pat. No. 10,774,141, issued Sep. 15, 2020, which is a continuation application of U.S. application Ser. No. 16/307,930, filed Dec. 6, 2018 (abandoned), which is the National Stage of International Application Number PCT/CN2017/087592, filed on Jun. 8, 2017, which claims priority of Chinese Patent Application Number 201610399254.4, filed on Jun. 8, 2016, the entire contents of each of which are incorporated herein by reference.

INCORPORATION BY REFERENCE

The instant application contains a Sequence Listing which has been submitted in ASCII format via EFS-Web and is hereby incorporated by reference in its entirety. Said ASCII copy was modified on Aug. 14, 2020, is named SUZ-001C1D1_Sequence_Listing.txt, and is 71,361 bytes in size.

TECHNICAL FIELD

The present invention relates to the field of biopharmaceutics. Particularly, the present invention relates to an antibody that is capable of binding to interleukin 4 (IL-4) receptor (IL-4R) and uses thereof.

BACKGROUND OF THE INVENTION

Interleukin-4 (IL-4) is a cytokine produced primarily by activated T cells, monocytes, basophils, mast cells, and eosinophils. IL-4 is involved in a variety of biological processes, and its biological effects known in the art include stimulating the proliferation of activated B cells and T cells and the differentiation of CD4+ T cells into type II helper T cells. What's more, studies have shown that IL-4 has multiple effects in mediating immune responses to diseases such as allergic diseases, autoimmune diseases, infectious diseases and tumors, and has therapeutic effects on tumors, autoimmune diseases and infectious diseases and the like. Meanwhile, IL-4 can also regulate immune response to vaccine. Therefore, IL-4 has always been one hot area for research attracting extensive attentions.

IL-13 is also a cytokine produced by activated T cells, which has different functions in different types of cells, such as monocytes, B cells, mast cells and keratinocytes. IL-13 can inhibit the release of inflammatory cytokines and chemokines from monocytes, induce the proliferation and differentiation of B cells, and promote the synthesis of IgE. IL-13 and IL-4 share many common properties in terms of biological functions, including inhibiting the release of inflammatory mediators from monocytes, inducing dendritic-like development of macrophages, promoting the expression of CD23 on the surface of monocytes and stimulating the synthesis of immunoglobulins by B cells. At the same time, IL-13 also has its own biological features, mainly including: promoting the differentiation of human monocytes and changes of antigens on cell surface; inducing the proliferation and differentiation of B cells, and promoting the secretion of antibodies from B cells; regulating the synthesis of IgE, thereby being associated with allergic reactions in the body; inhibiting the growth of tumor cells; inhibiting the replication of HIV; and the like.

The biological activity of IL-4 is mediated by a specific IL-4 receptor on cell surface (IL-4R, which is called "hIL-4R" in human). Human IL-4R is a heterodimer formed by two polypeptide chains, in which the alpha chain (hIL-4Rα, UniProtKB: P24394) has a high affinity for IL-4. And studies have shown that the cell surface receptor alpha chain of IL-13 (IL-13Rα chain) also forms another form of IL-4R complex with IL-4Rα chain. Since the IL-4Rα chain in the IL-4R complex plays a leading role in binding to IL-4 and other cytokines are involved, the IL-4Rα chain is currently being studied as a major target. What's more, human monoclonal antibodies against the IL-4Rα chain have been clinically proven to be effective in relieving and treating conditions such as asthma, eczema, atopic dermatitis and the like.

Human interleukin-4 receptor is known to produce a soluble form of protein (shIL-4Rα, SEQ ID NO: 94) that inhibits cell proliferation mediated by IL-4 and IL-5 up-regulation mediated by T cells. Two forms of the receptor are associated with allergic reaction, which manifests as diseases like allergic rhinitis, sinusitis, asthma, eczema and so on. Therefore, blocking antibodies that target the protein can help treat and relieve said diseases.

Asthma is a chronic airway inflammatory disease, in which many inflammatory cells, such as eosinophils, mast cells and lymphocytes are involved, and its specific pathogenesis is still unclear. Since cytokines such as IL-4 play an important role in the occurrence and development of bronchial asthma, the development of antibodies specific for IL-4 is one of the effective ways to treat asthma. Inhibition of IL-4/IL-4Rα can have an effective immunomodulatory effect on asthma.

Allergic rhinitis (AR) has a pathogenesis much in common with that of asthma, and it and asthma both belong to type I allergy. Meanwhile, studies have found that IL-4, IL-17 and IgE play an important role in the pathogenesis of allergic rhinitis. So far, drug therapy is the focus of AR treatment, in which intranasal corticosteroids and antihistamines are at the core position.

Atopic dermatitis (AD), also known as heterotopic dermatitis or hereditary allergic dermatitis, is a common dermatological disease that is mostly seen in children and adolescents, and is often complicated with certain hereditary allergic diseases such as allergic rhinitis, asthma and the like. The involvement of immunological factors such as IL-4 and IL-13 are one of the main pathogenesis.

Eosinophilic esophagitis (EoE) is a chronic immune inflammatory disease characterized by infiltration of eosinophils (EOS) in all layers of esophagus. The onset of EoE is associated with dysfunction of Th2 cells. At present, protocols with high specificity, such as novel biological agent anti-IL-5 (such as mepolizumab) have become hotspots in research. Although immune-modulating therapy has achieved results in animal models, explorations are still needed in human clinical trials. Medicaments such as PGD2 inhibitors, anti-TNF-α, and anti-IL-13 are under investigation at present.

Monoclonal antibody medicaments targeting the hIL-4R have now entered clinical trials, such as Dupilumab, which has shown good efficacy in phase II clinical trial of atopic dermatitis. In addition to Dupilumab, other monoclonal antibodies against hIL-4R have been claimed in patent applications by companies, for example U.S. Pat. Nos. 7,186,809 and 7,638,606.

SUMMARY OF THE INVENTION

The present invention provides an antibody specific for IL-4R through antibody screening and optimization, and the antibody can serve as a blocking agent for the binding of IL-4 to IL-4R, and can be used for treating inflammation or allergic diseases by binding to IL-4R.

With reference to the numbering of amino acid residues of the sequence as set forth in SEQ ID NO: 58, the antibody of the present invention has a serine at position 31 (31Ser) of the light chain variable region comprised therein, and with reference to the numbering of amino acid residues of the sequence as set forth in SEQ ID NO: 93, the antibody has an aspartic acid at position 103 (103Asp), and a tyrosine at position 104 (104Tyr) of the heavy chain variable region comprised therein. Wherein, the 31Ser is located in CDR1 of the light chain variable region of the present antibody correspondingly, and the 103Asp and 104Tyr are located in the CDR3 of the heavy chain variable region of the present antibody correspondingly.

Preferably, the light chain variable region of the present antibody comprises CDR1 as set forth in SEQ ID NO: 2, and the heavy variable region of the antibody comprises CDR3 as set forth in SEQ ID NO: 19.

Preferably, the light chain variable region of the present antibody comprises a combination of CDR1, CDR2, and CDR3 selected from the group consisting of:

(1) CDR1 as set forth in SEQ ID NO: 2, CDR2 as set forth in SEQ ID NO: 3 and CDR3 as set forth in SEQ ID NO: 5;

(2) CDR1 as set forth in SEQ ID NO: 2, CDR2 as set forth in SEQ ID NO: 4 and CDR3 as set forth in SEQ ID NO: 5;

(3) CDR1 as set forth in SEQ ID NO: 2, CDR2 as set forth in SEQ ID NO: 3 and CDR3 as set forth in SEQ ID NO: 6;

(4) CDR1 as set forth in SEQ ID NO: 2, CDR2 as set forth in SEQ ID NO: 3 and CDR3 as set forth in SEQ ID NO: 7;

(5) CDR1 as set forth in SEQ ID NO: 2, CDR2 as set forth in SEQ ID NO: 3 and CDR3 as set forth in SEQ ID NO: 8;

(6) CDR1 as set forth in SEQ ID NO: 2, CDR2 as set forth in SEQ ID NO: 4 and CDR3 as set forth in SEQ ID NO: 6;

(7) CDR1 as set forth in SEQ ID NO: 2, CDR2 as set forth in SEQ ID NO: 4 and CDR3 as set forth in SEQ ID NO: 7; and (8) CDR1 as set forth in SEQ ID NO: 2, CDR2 as set forth in SEQ ID NO: 4 and CDR3 as set forth in SEQ ID NO: 8; and the heavy chain variable region of the present antibody comprises a combination of CDR1, CDR2, and CDR3 selected from the group consisting of:

(1) CDR1 as set forth in SEQ ID NO: 14, CDR2 as set forth in SEQ ID NO: 17 and CDR3 as set forth in SEQ ID NO: 19;

(2) CDR1 as set forth in SEQ ID NO: 14, CDR2 as set forth in SEQ ID NO: 18 and CDR3 as set forth in SEQ ID NO: 19;

(3) CDR1 as set forth in SEQ ID NO: 15, CDR2 as set forth in SEQ ID NO: 17 and CDR3 as set forth in SEQ ID NO: 19;

(4) CDR1 as set forth in SEQ ID NO: 15, CDR2 as set forth in SEQ ID NO:
18 and CDR3 as set forth in SEQ ID NO: 19;

(5) CDR1 as set forth in SEQ ID NO: 16, CDR2 as set forth in SEQ ID NO: 18 and CDR3 as set forth in SEQ ID NO: 19; and (6) CDR1 as set forth in SEQ ID NO: 16, CDR2 as set forth in SEQ ID NO: 17 and CDR3 as set forth in SEQ ID NO: 19.

More preferably, the present invention antibody comprises a light chain variable region selected from the amino acid sequences shown in the following sequences: SEQ ID NO: 40, SEQ ID NO: 41, SEQ ID NO: 44, SEQ ID NO: 45, SEQ ID NO: 46, SEQ ID NO: 47, SEQ ID NO: 49, SEQ ID NO: 50, SEQ ID NO: 51, SEQ ID NO: 54, SEQ ID NO: 55 and SEQ ID NO: 57, and the antibody comprises a heavy chain variable region selected from the amino acid sequences shown in the following sequences: SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 91 and SEQ ID NO: 92.

Further preferably, the present antibody comprises a combination of a light chain variable region and a heavy chain variable region selected from the group consisting of:

(1) a light chain variable region as set forth in SEQ ID NO: 57 and a heavy chain variable region as set forth in SEQ ID NO: 62;

(2) a light chain variable region as set forth in SEQ ID NO: 57 and a heavy chain variable region as set forth in SEQ ID NO: 63;

(3) a light chain variable region as set forth in SEQ ID NO: 57 and a heavy chain variable region as set forth in SEQ ID NO: 59;

(4) a light chain variable region as set forth in SEQ ID NO: 57 and a heavy chain variable region as set forth in SEQ ID NO: 60;

(5) a light chain variable region as set forth in SEQ ID NO: 57 and a heavy chain variable region as set forth in SEQ ID NO: 61;

(6) a light chain variable region as set forth in SEQ ID NO: 57 and a heavy chain variable region as set forth in SEQ ID NO: 67;

(7) a light chain variable region as set forth in SEQ ID NO: 57 and a heavy chain variable region as set forth in SEQ ID NO: 65;

(8) a light chain variable region as set forth in SEQ ID NO: 57 and a heavy chain variable region as set forth in SEQ ID NO: 66;

(9) a light chain variable region as set forth in SEQ ID NO: 57 and a heavy chain variable region as set forth in SEQ ID NO: 64;

(10) a light chain variable region as set forth in SEQ ID NO: 57 and a heavy chain variable region as set forth in SEQ ID NO: 91;

(11) a light chain variable region as set forth in SEQ ID NO: 57 and a heavy chain variable region as set forth in SEQ ID NO: 74;

(12) a light chain variable region as set forth in SEQ ID NO: 57 and a heavy chain variable region as set forth in SEQ ID NO: 75;

(13) a light chain variable region as set forth in SEQ ID NO: 57 and a heavy chain variable region as set forth in SEQ ID NO: 76;

(14) a light chain variable region as set forth in SEQ ID NO: 57 and a heavy chain variable region as set forth in SEQ ID NO: 77;

(15) a light chain variable region as set forth in SEQ ID NO: 57 and a heavy chain variable region as set forth in SEQ ID NO: 78;

(16) a light chain variable region as set forth in SEQ ID NO: 57 and a heavy chain variable region as set forth in SEQ ID NO: 80;

(17) a light chain variable region as set forth in SEQ ID NO: 40 and a heavy chain variable region as set forth in SEQ ID NO: 92;

(18) a light chain variable region as set forth in SEQ ID NO: 41 and a heavy chain variable region as set forth in SEQ ID NO: 92;

(19) a light chain variable region as set forth in SEQ ID NO: 44 and a heavy chain variable region as set forth in SEQ ID NO: 92;
(20) a light chain variable region as set forth in SEQ ID NO: 44 and a heavy chain variable region as set forth in SEQ ID NO: 62;
(21) a light chain variable region as set forth in SEQ ID NO: 44 and a heavy chain variable region as set forth in SEQ ID NO: 91;
(22) a light chain variable region as set forth in SEQ ID NO: 49 and a heavy chain variable region as set forth in SEQ ID NO: 92;
(23) a light chain variable region as set forth in SEQ ID NO: 50 and a heavy chain variable region as set forth in SEQ ID NO: 92;
(24) a light chain variable region as set forth in SEQ ID NO: 45 and a heavy chain variable region as set forth in SEQ ID NO: 92;
(25) a light chain variable region as set forth in SEQ ID NO: 46 and a heavy chain variable region as set forth in SEQ ID NO: 92;
(26) a light chain variable region as set forth in SEQ ID NO: 47 and a heavy chain variable region as set forth in SEQ ID NO: 92;
(27) a light chain variable region as set forth in SEQ ID NO: 55 and a heavy chain variable region as set forth in SEQ ID NO: 92;
(28) a light chain variable region as set forth in SEQ ID NO: 55 and a heavy chain variable region as set forth in SEQ ID NO: 62;
(29) a light chain variable region as set forth in SEQ ID NO: 55 and a heavy chain variable region as set forth in SEQ ID NO: 91;
(30) a light chain variable region as set forth in SEQ ID NO: 54 and a heavy chain variable region as set forth in SEQ ID NO: 92;
(31) a light chain variable region as set forth in SEQ ID NO: 54 and a heavy chain variable region as set forth in SEQ ID NO: 62;
(32) a light chain variable region as set forth in SEQ ID NO: 54 and a heavy chain variable region as set forth in SEQ ID NO: 91; and
(33) a light chain variable region as set forth in SEQ ID NO: 51 and a heavy chain variable region as set forth in SEQ ID NO: 92.

In another aspect, the present invention provides an antibody that can bind to Interleukin 4 (IL-4) receptor (IL-4R). The antibody comprises a light chain variable region (VL), and the light chain variable region comprises a combination of CDR1, CDR2 and CDR3 selected from the group consisting of:
(1) CDR1 as set forth in SEQ ID NO: 1, CDR2 as set forth in SEQ ID NO: 3 and CDR3 as set forth in SEQ ID NO: 5;
(2) CDR1 as set forth in SEQ ID NO: 2, CDR2 as set forth in SEQ ID NO: 3 and CDR3 as set forth in SEQ ID NO: 5;
(3) CDR1 as set forth in SEQ ID NO: 2, CDR2 as set forth in SEQ ID NO: 4 and CDR3 as set forth in SEQ ID NO: 5;
(4) CDR1 as set forth in SEQ ID NO: 1, CDR2 as set forth in SEQ ID NO: 4 and CDR3 as set forth in SEQ ID NO: 5;
(5) CDR1 as set forth in SEQ ID NO: 2, CDR2 as set forth in SEQ ID NO: 3 and CDR3 as set forth in SEQ ID NO: 6;
(6) CDR1 as set forth in SEQ ID NO: 2, CDR2 as set forth in SEQ ID NO: 3 and CDR3 as set forth in SEQ ID NO: 7;
(7) CDR1 as set forth in SEQ ID NO: 2, CDR2 as set forth in SEQ ID NO: 3 and CDR3 as set forth in SEQ ID NO: 8;
(8) CDR1 as set forth in SEQ ID NO: 1, CDR2 as set forth in SEQ ID NO: 3 and CDR3 as set forth in SEQ ID NO: 6;
(9) CDR1 as set forth in SEQ ID NO: 2, CDR2 as set forth in SEQ ID NO: 4 and CDR3 as set forth in SEQ ID NO: 6;
(10) CDR1 as set forth in SEQ ID NO: 2, CDR2 as set forth in SEQ ID NO: 4 and CDR3 as set forth in SEQ ID NO: 8;
(11) CDR1 as set forth in SEQ ID NO: 1, CDR2 as set forth in SEQ ID NO: 4 and CDR3 as set forth in SEQ ID NO: 8 and
(12) CDR1 as set forth in SEQ ID NO: 1, CDR2 as set forth in SEQ ID NO: 3 and CDR3 as set forth in SEQ ID NO: 8;

and/or the antibody comprises a heavy chain variable region (VH), and the heavy chain variable region comprises a combination of CDR1, CDR2 and CDR3 selected from the group consisting of:
(1) CDR1 as set forth in SEQ ID NO: 14, CDR2 as set forth in SEQ ID NO: 17 and CDR3 as set forth in SEQ ID NO: 19;
(2) CDR1 as set forth in SEQ ID NO: 14, CDR2 as set forth in SEQ ID NO: 18 and CDR3 as set forth in SEQ ID NO: 19;
(3) CDR1 as set forth in SEQ ID NO: 14, CDR2 as set forth in SEQ ID NO: 17 and CDR3 as set forth in SEQ ID NO: 20;
(4) CDR1 as set forth in SEQ ID NO: 14, CDR2 as set forth in SEQ ID NO: 18 and CDR3 as set forth in SEQ ID NO: 20;
(5) CDR1 as set forth in SEQ ID NO: 15, CDR2 as set forth in SEQ ID NO: 17 and CDR3 as set forth in SEQ ID NO: 19;
(6) CDR1 as set forth in SEQ ID NO: 16, CDR2 as set forth in SEQ ID NO: 17 and CDR3 as set forth in SEQ ID NO: 19; and
(7) CDR1 as set forth in SEQ ID NO: 14, CDR2 as set forth in SEQ ID NO: 18 and CDR3 as set forth in SEQ ID NO: 19.

Further, with regard to framework regions of the antibody of the present invention as described above, the light chain variable region of the present antibody preferably comprises a combination of FR1, FR2, FR3 and FR4 selected from the group consisting of:
(1) FR1 as set forth in SEQ ID NO: 9, FR2 as set forth in SEQ ID NO: 10, FR3 as set forth in SEQ ID NO: 12 and FR4 as set forth in SEQ ID NO: 13; and
(2) FR1 as set forth in SEQ ID NO: 9, FR2 as set forth in SEQ ID NO: 11, FR3 as set forth in SEQ ID NO: 12 and FR4 as set forth in SEQ ID NO: 13.

Preferably, the heavy chain variable region of the antibody comprises a combination of FR1, FR2, FR3 and FR4 selected from the group consisting of:
(1) FR1 as set forth in SEQ ID NO: 21, FR2 as set forth in SEQ ID NO: 32, FR3 as set forth in SEQ ID NO: 34 and FR4 as set forth in SEQ ID NO: 38;
(2) FR1 as set forth in SEQ ID NO: 22, FR2 as set forth in SEQ ID NO: 32, FR3 as set forth in SEQ ID NO: 34 and FR4 as set forth in SEQ ID NO: 38;
(3) FR1 as set forth in SEQ ID NO: 23, FR2 as set forth in SEQ ID NO: 32, FR3 as set forth in SEQ ID NO: 34 and FR4 as set forth in SEQ ID NO: 38;
(4) FR1 as set forth in SEQ ID NO: 24, FR2 as set forth in SEQ ID NO: 32, FR3 as set forth in SEQ ID NO: 34 and FR4 as set forth in SEQ ID NO: 38;
(5) FR1 as set forth in SEQ ID NO: 24, FR2 as set forth in SEQ ID NO: 32, FR3 as set forth in SEQ ID NO: 35 and FR4 as set forth in SEQ ID NO: 38;

(6) FR1 as set forth in SEQ ID NO: 25, FR2 as set forth in SEQ ID NO: 32, FR3 as set forth in SEQ ID NO: 34 and FR4 as set forth in SEQ ID NO: 38;

(7) FR1 as set forth in SEQ ID NO: 26, FR2 as set forth in SEQ ID NO: 32, FR3 as set forth in SEQ ID NO: 34 and FR4 as set forth in SEQ ID NO: 38;

(8) FR1 as set forth in SEQ ID NO: 27, FR2 as set forth in SEQ ID NO: 32, FR3 as set forth in SEQ ID NO: 34 and FR4 as set forth in SEQ ID NO: 38;

(9) FR1 as set forth in SEQ ID NO: 29, FR2 as set forth in SEQ ID NO: 32, FR3 as set forth in SEQ ID NO: 34 and FR4 as set forth in SEQ ID NO: 38;

(10) FR1 as set forth in SEQ ID NO: 30, FR2 as set forth in SEQ ID NO: 32, FR3 as set forth in SEQ ID NO: 34 and FR4 as set forth in SEQ ID NO: 38;

(11) FR1 as set forth in SEQ ID NO: 24, FR2 as set forth in SEQ ID NO: 33, FR3 as set forth in SEQ ID NO: 34 and FR4 as set forth in SEQ ID NO: 38;

(12) FR1 as set forth in SEQ ID NO: 24, FR2 as set forth in SEQ ID NO: 32, FR3 as set forth in SEQ ID NO: 36 and FR4 as set forth in SEQ ID NO: 38;

(13) FR1 as set forth in SEQ ID NO: 24, FR2 as set forth in SEQ ID NO: 32, FR3 as set forth in SEQ ID NO: 37 and FR4 as set forth in SEQ ID NO: 38;

(14) FR1 as set forth in SEQ ID NO: 31, FR2 as set forth in SEQ ID NO: 32, FR3 as set forth in SEQ ID NO: 34 and FR4 as set forth in SEQ ID NO: 38;

(15) FR1 as set forth in SEQ ID NO: 27, FR2 as set forth in SEQ ID NO: 32, FR3 as set forth in SEQ ID NO: 35 and FR4 as set forth in SEQ ID NO: 38;

(16) FR1 as set forth in SEQ ID NO: 26, FR2 as set forth in SEQ ID NO: 32, FR3 as set forth in SEQ ID NO: 35 and FR4 as set forth in SEQ ID NO: 38;

(17) FR1 as set forth in SEQ ID NO: 25, FR2 as set forth in SEQ ID NO: 32, FR3 as set forth in SEQ ID NO: 35 and FR4 as set forth in SEQ ID NO: 38;

(18) FR1 as set forth in SEQ ID NO: 28, FR2 as set forth in SEQ ID NO: 32, FR3 as set forth in SEQ ID NO: 35 and FR4 as set forth in SEQ ID NO: 38;

(19) FR1 as set forth in SEQ ID NO: 28, FR2 as set forth in SEQ ID NO: 32, FR3 as set forth in SEQ ID NO: 34 and FR4 as set forth in SEQ ID NO: 38;

(20) FR1 as set forth in SEQ ID NO: 23, FR2 as set forth in SEQ ID NO: 32, FR3 as set forth in SEQ ID NO: 35 and FR4 as set forth in SEQ ID NO: 38;

(21) FR1 as set forth in SEQ ID NO: 22, FR2 as set forth in SEQ ID NO: 32, FR3 as set forth in SEQ ID NO: 35 and FR4 as set forth in SEQ ID NO: 38; and

(22) FR1 as set forth in SEQ ID NO: 21, FR2 as set forth in SEQ ID NO: 32, FR3 as set forth in SEQ ID NO: 35 and FR4 as set forth in SEQ ID NO: 38.

According to the domain composition of a light chain variable region and a heavy chain variable region of an antibody known in the art, the light chain variable region or the heavy chain variable region of present antibody comprises the above domain components in an order of FR1-CDR1-FR2-CDR2-FR3-CDR3-FR4, or comprises the above domain components in an order of (X)n-FR1-(X)n-CDR1-(X)n-FR2-(X)n-CDR2-(X)n-FR3-(X)n-CDR3-(X)n-FR4-(X)n, in which, X is any amino acid residue, and n is zero or an integer greater than zero.

Preferably, the antibody provided by the present invention comprises a light chain variable region selected from the amino acid sequences shown in the following sequences:

SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57 and SEQ ID NO: 58;

and/or the antibody provided by the present invention comprises a heavy chain variable region selected from the amino acid sequences shown in the following sequences:

SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92 and SEQ ID NO: 93.

According to particular embodiments of the present invention, the antibody provided by the present invention comprises a combination of a light chain variable region and a heavy chain variable region selected from the group consisting of:

(1) a light chain variable region as set forth in SEQ ID NO: 57 and a heavy chain variable region as set forth in SEQ ID NO: 62;

(2) a light chain variable region as set forth in SEQ ID NO: 57 and a heavy chain variable region as set forth in SEQ ID NO: 63;

(3) a light chain variable region as set forth in SEQ ID NO: 57 and a heavy chain variable region as set forth in SEQ ID NO: 59;

(4) a light chain variable region as set forth in SEQ ID NO: 57 and a heavy chain variable region as set forth in SEQ ID NO: 60;

(5) a light chain variable region as set forth in SEQ ID NO: 57 and a heavy chain variable region as set forth in SEQ ID NO: 61;

(6) a light chain variable region as set forth in SEQ ID NO: 57 and a heavy chain variable region as set forth in SEQ ID NO: 67;

(7) a light chain variable region as set forth in SEQ ID NO: 57 and a heavy chain variable region as set forth in SEQ ID NO: 65;

(8) a light chain variable region as set forth in SEQ ID NO: 57 and a heavy chain variable region as set forth in SEQ ID NO: 66;

(9) a light chain variable region as set forth in SEQ ID NO: 57 and a heavy chain variable region as set forth in SEQ ID NO: 64;

(10) a light chain variable region as set forth in SEQ ID NO: 57 and a heavy chain variable region as set forth in SEQ ID NO: 68;

(11) a light chain variable region as set forth in SEQ ID NO: 57 and a heavy chain variable region as set forth in SEQ ID NO: 69;

(12) a light chain variable region as set forth in SEQ ID NO: 57 and a heavy chain variable region as set forth in SEQ ID NO: 70;

(13) a light chain variable region as set forth in SEQ ID NO: 57 and a heavy chain variable region as set forth in SEQ ID NO: 71;

(14) a light chain variable region as set forth in SEQ ID NO: 57 and a heavy chain variable region as set forth in SEQ ID NO: 72;

(15) a light chain variable region as set forth in SEQ ID NO: 57 and a heavy chain variable region as set forth in SEQ ID NO: 73;
(16) a light chain variable region as set forth in SEQ ID NO: 57 and a heavy chain variable region as set forth in SEQ ID NO: 89;
(17) a light chain variable region as set forth in SEQ ID NO: 57 and a heavy chain variable region as set forth in SEQ ID NO: 88;
(18) a light chain variable region as set forth in SEQ ID NO: 57 and a heavy chain variable region as set forth in SEQ ID NO: 87;
(19) a light chain variable region as set forth in SEQ ID NO: 57 and a heavy chain variable region as set forth in SEQ ID NO: 86;
(20) a light chain variable region as set forth in SEQ ID NO: 57 and a heavy chain variable region as set forth in SEQ ID NO: 83;
(21) a light chain variable region as set forth in SEQ ID NO: 57 and a heavy chain variable region as set forth in SEQ ID NO: 82;
(22) a light chain variable region as set forth in SEQ ID NO: 57 and a heavy chain variable region as set forth in SEQ ID NO: 81;
(23) a light chain variable region as set forth in SEQ ID NO: 57 and a heavy chain variable region as set forth in SEQ ID NO: 85;
(24) a light chain variable region as set forth in SEQ ID NO: 57 and a heavy chain variable region as set forth in SEQ ID NO: 84;
(25) a light chain variable region as set forth in SEQ ID NO: 57 and a heavy chain variable region as set forth in SEQ ID NO: 91;
(26) a light chain variable region as set forth in SEQ ID NO: 57 and a heavy chain variable region as set forth in SEQ ID NO: 90;
(27) a light chain variable region as set forth in SEQ ID NO: 57 and a heavy chain variable region as set forth in SEQ ID NO: 74;
(28) a light chain variable region as set forth in SEQ ID NO: 57 and a heavy chain variable region as set forth in SEQ ID NO: 75;
(29) a light chain variable region as set forth in SEQ ID NO: 57 and a heavy chain variable region as set forth in SEQ ID NO: 76;
(30) a light chain variable region as set forth in SEQ ID NO: 57 and a heavy chain variable region as set forth in SEQ ID NO: 77;
(31) a light chain variable region as set forth in SEQ ID NO: 57 and a heavy chain variable region as set forth in SEQ ID NO: 78;
(32) a light chain variable region as set forth in SEQ ID NO: 57 and a heavy chain variable region as set forth in SEQ ID NO: 80;
(33) a light chain variable region as set forth in SEQ ID NO: 39 and a heavy chain variable region as set forth in SEQ ID NO: 92;
(34) a light chain variable region as set forth in SEQ ID NO: 40 and a heavy chain variable region as set forth in SEQ ID NO: 92;
(35) a light chain variable region as set forth in SEQ ID NO: 41 and a heavy chain variable region as set forth in SEQ ID NO: 92;
(36) a light chain variable region as set forth in SEQ ID NO: 42 and a heavy chain variable region as set forth in SEQ ID NO: 92;
(37) a light chain variable region as set forth in SEQ ID NO: 43 and a heavy chain variable region as set forth in SEQ ID NO: 92;
(38) a light chain variable region as set forth in SEQ ID NO: 44 and a heavy chain variable region as set forth in SEQ ID NO: 92;
(39) a light chain variable region as set forth in SEQ ID NO: 44 and a heavy chain variable region as set forth in SEQ ID NO: 62;
(40) a light chain variable region as set forth in SEQ ID NO: 44 and a heavy chain variable region as set forth in SEQ ID NO: 68;
(41) a light chain variable region as set forth in SEQ ID NO: 44 and a heavy chain variable region as set forth in SEQ ID NO: 72;
(42) a light chain variable region as set forth in SEQ ID NO: 44 and a heavy chain variable region as set forth in SEQ ID NO: 82;
(43) a light chain variable region as set forth in SEQ ID NO: 44 and a heavy chain variable region as set forth in SEQ ID NO: 85;
(44) a light chain variable region as set forth in SEQ ID NO: 44 and a heavy chain variable region as set forth in SEQ ID NO: 91;
(45) a light chain variable region as set forth in SEQ ID NO: 48 and a heavy chain variable region as set forth in SEQ ID NO: 92;
(46) a light chain variable region as set forth in SEQ ID NO: 49 and a heavy chain variable region as set forth in SEQ ID NO: 92;
(47) a light chain variable region as set forth in SEQ ID NO: 50 and a heavy chain variable region as set forth in SEQ ID NO: 92;
(48) a light chain variable region as set forth in SEQ ID NO: 45 and a heavy chain variable region as set forth in SEQ ID NO: 92;
(49) a light chain variable region as set forth in SEQ ID NO: 46 and a heavy chain variable region as set forth in SEQ ID NO: 92;
(50) a light chain variable region as set forth in SEQ ID NO: 47 and a heavy chain variable region as set forth in SEQ ID NO: 92;
(51) a light chain variable region as set forth in SEQ ID NO: 56 and a heavy chain variable region as set forth in SEQ ID NO: 92;
(52) a light chain variable region as set forth in SEQ ID NO: 55 and a heavy chain variable region as set forth in SEQ ID NO: 92;
(53) a light chain variable region as set forth in SEQ ID NO: 55 and a heavy chain variable region as set forth in SEQ ID NO: 62;
(54) a light chain variable region as set forth in SEQ ID NO: 55 and a heavy chain variable region as set forth in SEQ ID NO: 68;
(55) a light chain variable region as set forth in SEQ ID NO: 55 and a heavy chain variable region as set forth in SEQ ID NO: 72;
(56) a light chain variable region as set forth in SEQ ID NO: 55 and a heavy chain variable region as set forth in SEQ ID NO: 82;
(57) a light chain variable region as set forth in SEQ ID NO: 55 and a heavy chain variable region as set forth in SEQ ID NO: 85;
(58) a light chain variable region as set forth in SEQ ID NO: 55 and a heavy chain variable region as set forth in SEQ ID NO: 91;

(59) a light chain variable region as set forth in SEQ ID NO: 54 and a heavy chain variable region as set forth in SEQ ID NO: 92;

(60) a light chain variable region as set forth in SEQ ID NO: 54 and a heavy chain variable region as set forth in SEQ ID NO: 62;

(61) a light chain variable region as set forth in SEQ ID NO: 54 and a heavy chain variable region as set forth in SEQ ID NO: 68;

(62) a light chain variable region as set forth in SEQ ID NO: 54 and a heavy chain variable region as set forth in SEQ ID NO: 72;

(63) a light chain variable region as set forth in SEQ ID NO: 54 and a heavy chain variable region as set forth in SEQ ID NO: 82;

(64) a light chain variable region as set forth in SEQ ID NO: 54 and a heavy chain variable region as set forth in SEQ ID NO: 85;

(65) a light chain variable region as set forth in SEQ ID NO: 54 and a heavy chain variable region as set forth in SEQ ID NO: 91;

(66) a light chain variable region as set forth in SEQ ID NO: 53 and a heavy chain variable region as set forth in SEQ ID NO: 92;

(67) a light chain variable region as set forth in SEQ ID NO: 51 and a heavy chain variable region as set forth in SEQ ID NO: 92;

(68) a light chain variable region as set forth in SEQ ID NO: 52 and a heavy chain variable region as set forth in SEQ ID NO: 92;

(69) a light chain variable region as set forth in SEQ ID NO: 52 and a heavy chain variable region as set forth in SEQ ID NO: 62;

(70) a light chain variable region as set forth in SEQ ID NO: 52 and a heavy chain variable region as set forth in SEQ ID NO: 91;

(71) a light chain variable region as set forth in SEQ ID NO: 58 and a heavy chain variable region as set forth in SEQ ID NO: 92;

(72) a light chain variable region as set forth in SEQ ID NO: 57 and a heavy chain variable region as set forth in SEQ ID NO: 93;

(73) a light chain variable region as set forth in SEQ ID NO: 44 and a heavy chain variable region as set forth in SEQ ID NO: 93;

(74) a light chain variable region as set forth in SEQ ID NO: 58 and a heavy chain variable region as set forth in SEQ ID NO: 91;

(75) a light chain variable region as set forth in SEQ ID NO: 55 and a heavy chain variable region as set forth in SEQ ID NO: 93; and

(76) a light chain variable region as set forth in SEQ ID NO: 51 and a heavy chain variable region as set forth in SEQ ID NO: 93.

The antibody provided by the present invention is capable of binding to IL-4R and functions as an antagonist of IL-4R. Preferably, the antibody is capable of binding to IL-4Rα, preferably to mammal IL-4Rα, more preferably to human IL-4Rα, even more preferably to human soluble IL-4Rα.

Binding affinity of the antibody provided by the present invention to IL-4Rα can be determined by method Biacore or ELISA. The antibody is determined to bind IL-4Rα with an affinity of less than 100 nM, less than 10 nM, less than 1 nM, less than 0.5 nM, and even less than 0.1 nM.

Under the same conditions, the ratio of the expression level of the antibody provided by the present invention to that of reference antibody is 0.1-3:1, preferably 0.3-3:1, more preferably 0.4-3:1, still preferably 0.5-3:1, still more preferably 0.6-3:1, further preferably 0.7-3:1, further more preferably 1-3:1.

In terms of antibody type, the antibody provided by the present invention can be a monoclonal antibody, fully or partially humanized antibody or chimeric antibody.

Or preferably, the antibody is an immunoglobulin, preferably IgA, IgD, IgE, IgG or IgM, more preferably IgG1, IgG2, IgG3 or IgG4 subtype, further more preferably IgG2 or IgG4 subtype.

In further another aspect, the invention provides a fusion protein or conjugate comprising the antibody of the present invention. The fusion protein or conjugate may further comprises cell surface receptor, active protein or active polypeptide, small molecule compound such as amino acid and saccharide, small molecule polymer or other parts chemically modifying the antibody, etc., bound to the present antibody by chemical or physical means.

In still another aspect, the present invention provides a nucleic acid sequence that can encode the heavy chain variable region and/or light chain variable region of the antibody provided by the present invention.

Preferably, the nucleic acid sequence can encode the heavy chain and/or light chain of the antibody provided by the present invention.

In yet another aspect, the present invention also provides a vector comprising the nucleic acid sequence provided by the present invention. The vector may be an eukaryotic expression vector, a prokaryotic expression vector, an artificial chromosome, a phage vector or the like.

The vector or nucleic acid sequence as described above can be used to transform or transfect host cells for purposes of preservation or antibody expression, and the like. Accordingly, the invention also provides a host cell transformed or transfected with the nucleic acid sequence or the vector. The host cell can be any prokaryotic or eukaryotic cell, such as a bacterial or insect, fungal, plant or animal cell.

The antibody provided by the present invention can be obtained through any method known in the art. For example, the heavy chain variable region and/or the light chain variable region of the antibody, or the heavy and/or light chain of the antibody can be obtained from the nucleic acid sequence provided by the present invention firstly, and then assembled into the antibody with any other domain of the antibody; or, the host cell provided by the present invention is cultured under conditions that the host cell is allowed to express the heavy chain variable region and/or the light chain variable region of the antibody or the heavy and/or light chain of the antibody for assembly into the antibody.

Optionally, the method further includes a step of recovering the produced antibody.

The antibody, fusion protein or conjugate, nucleic acid sequence, vector or host cell provided by the present invention or antibody produced by the method as described above may be contained in a pharmaceutical composition, and more particularly, in a pharmaceutical preparation for various purposes as actually needed. Therefore, in a further aspect, the present invention also provides a pharmaceutical composition comprising the antibody, fusion protein or conjugate, nucleic acid sequence, vector, host cell of the present invention and/or antibody produced by the method as described above.

Optionally, the pharmaceutical composition can be a pharmaceutical preparation. The pharmaceutical preparation is, for example, an injection.

The pharmaceutical composition or pharmaceutical preparation may further comprises a pharmaceutically acceptable carrier or excipient, depending on the particular dosage form.

In the pharmaceutical composition or pharmaceutical preparation, at least one of the following medicaments may also be contained: antiasthmatics such as albuterol etc., antihistamines such as loratadine etc., Immunosuppressive agents such as tacrolimus and pimecrolimus etc., M receptor blockers such as ipratropium bromide etc., leukotriene receptor blockers such as montelukast etc., phosphodiesterase inhibitors such as theophylline etc., non-steroidal anti-inflammatory drugs such as 5-aminosalicylic acid etc., hormones such as beclomethasone and budesonide etc., that is to say the antibody, fusion protein or conjugate, nucleic acid sequence, vector, host cell provided by the preset invention or antibody produced by the present method as described above may be used in combination with other medicaments as required.

In still further another aspect, the present invention also provides use of the antibody, fusion protein or conjugate, nucleic acid sequence, vector, host cell or antibody produced by the method for manufacturing a medicament for the prevention, treatment or amelioration of inflammation or allergic disease.

Preferably, the inflammation or allergic disease includes autoimmune disease, such as allergic dermatitis, asthma, eosinophilic esophagitis, eczema, allergic rhinitis, nasal polyp, rheumatoid arthritis and the like.

In still yet another aspect, the present invention provides a method of preventing, treating or ameliorating inflammation or allergic disease, and the method includes administering to a subject in need thereof the antibody, fusion protein or conjugate, nucleic acid sequence, vector, host cell provided by the present invention and/or antibody produced by the present method.

Preferably, the subject is a mammal, more preferably, the subject is a human.

Preferably, the inflammation or allergic disease includes autoimmune disease, such as allergic dermatitis, asthma, eosinophilic esophagitis, eczema, allergic rhinitis, nasal polyp, rheumatoid arthritis and the like.

Other medicaments can be used in combination to prevent, treat or ameliorate inflammation or allergic disease, for example, the method further includes administering to a subject in need thereof at least one medicament selected from the group consisting of: antiasthmatics such as albuterol etc., antihistamines such as loratadine etc., Immunosuppressive agents such as tacrolimus and pimecrolimus etc., M receptor blockers such as ipratropium bromide etc., leukotriene receptor blockers such as montelukast etc., phosphodiesterase inhibitors such as theophylline etc., non-steroidal anti-inflammatory drugs such as 5-aminosalicylic acid, etc., hormones such as beclomethasone and budesonide etc.

Preferably, the medicament is administered simultaneously or sequentially with the antibody, fusion protein or conjugate, nucleic acid sequence, vector, host cell provided by the present invention and/or antibody produced by the present method.

In further yet another aspect, the present invention also provides a kit, and the kit comprises the antibody, fusion protein or conjugate, nucleic acid sequence, vector, host cell provided by the present invention and/or antibody produced by the present method.

BRIEF DESCRIPTION OF THE DRAWINGS

The invention may be better understood by combination with the non-limiting embodiments of the present invention and the accompanying drawings, in which.

DETAILED DESCRIPTION OF PREFERRED EMBODIMENTS

Figure 1:
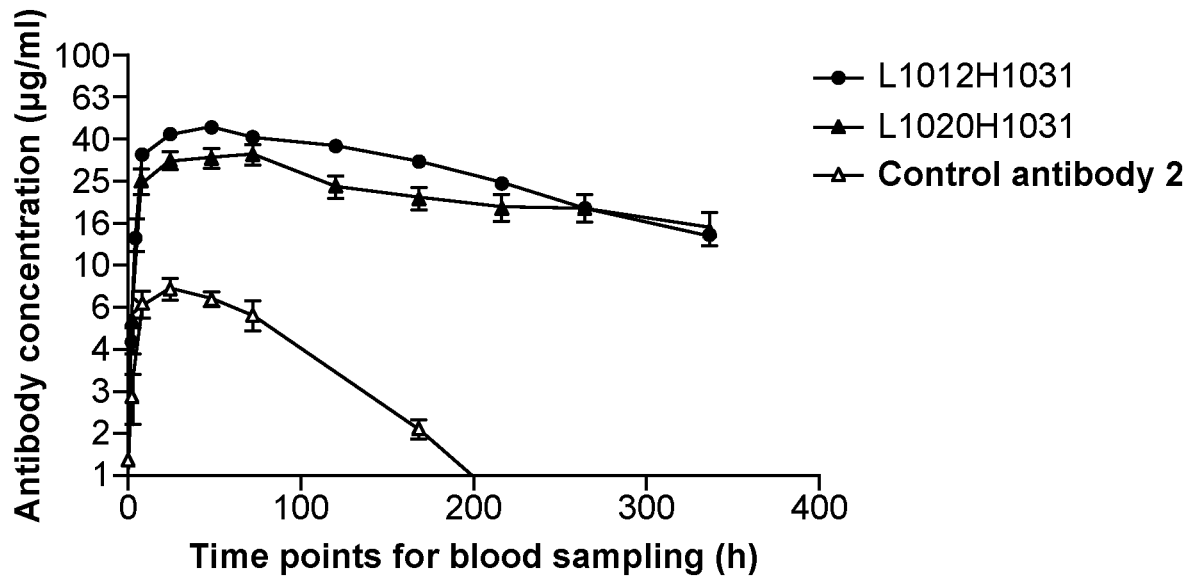
FIG. 1 shows the pharmacokinetic curves of the antibodies of the present invention in mouse.

The present invention will be further described in detail in combination with the particular embodiments hereinafter. It will be appreciated by those skilled in the art that the embodiments provided are only used to illustrate the present invention, rather than limiting the scope of the present invention in any way.

Experimental methods in the following Examples are all conventional methods, unless particularly stated. Raw materials used in the following Examples are commercially available from conventional biochemical reagent stores, unless particularly stated.

In the following Examples, the antibodies shown in Table 1 and their effects are exemplarily provided and verified.

TABLE 1

Exemplary antibodies provided by the present invention

| Number | SED ID NOs of the light chain variable region and the heavy chain variable region |
|---|---|
| L1000H1007 | SEQ ID NO:: 57 + SEQ ID NO:: 62 |
| L1000H1008 | SEQ ID NO:: 57 + SEQ ID NO:: 63 |
| L1000H1009 | SEQ ID NO:: 57 + SEQ ID NO: 59 |
| L1000H1010 | SEQ ID NO: 57 + SEQ ID NO: 60 |
| L1000H1011 | SEQ ID NO: 57 + SEQ ID NO: 61 |
| L1000H1012 | SEQ ID NO: 57 + SEQ ID NO: 67 |

TABLE 1-continued

Exemplary antibodies provided by the present invention

| Number | SED ID NOs of the light chain variable region and the heavy chain variable region |
|---|---|
| L1000H1013 | SEQ ID NO: 57 + SEQ ID NO: 65 |
| L1000H1014 | SEQ ID NO: 57 + SEQ ID NO: 66 |
| L1000H1015 | SEQ ID NO: 57 + SEQ ID NO: 64 |
| L1000H1016 | SEQ ID NO: 57 + SEQ ID NO: 68 |
| L1000H1017 | SEQ ID NO: 57 + SEQ ID NO: 69 |
| L1000H1018 | SEQ ID NO: 57 + SEQ ID NO: 70 |
| L1000H1019 | SEQ ID NO: 57 + SEQ ID NO: 71 |
| L1000H1020 | SEQ ID NO: 57 + SEQ ID NO: 72 |
| L1000H1021 | SEQ ID NO: 57 + SEQ ID NO: 73 |
| L1000H1022 | SEQ ID NO: 57 + SEQ ID NO: 89 |
| L1000H1023 | SEQ ID NO: 57 + SEQ ID NO: 88 |
| L1000H1024 | SEQ ID NO: 57 + SEQ ID NO: 87 |
| L1000H1025 | SEQ ID NO: 57 + SEQ ID NO: 86 |
| L1000H1026 | SEQ ID NO: 57 + SEQ ID NO: 83 |
| L1000H1027 | SEQ ID NO: 57 + SEQ ID NO: 82 |
| L1000H1028 | SEQ ID NO: 57 + SEQ ID NO: 81 |
| L1000H1029 | SEQ ID NO: 57 + SEQ ID NO: 85 |
| L1000H1030 | SEQ ID NO: 57 + SEQ ID NO: 84 |
| L1000H1031 | SEQ ID NO: 57 + SEQ ID NO: 91 |
| L1000H1032 | SEQ ID NO: 57 + SEQ ID NO: 90 |
| L1000H1033 | SEQ ID NO: 57 + SEQ ID NO: 74 |
| L1000H1034 | SEQ ID NO: 57 + SEQ ID NO: 75 |
| L1000H1035 | SEQ ID NO: 57 + SEQ ID NO: 76 |
| L1000H1036 | SEQ ID NO: 57 + SEQ ID NO: 77 |
| L1000H1037 | SEQ ID NO: 57 + SEQ ID NO: 78 |
| L1000H1038 | SEQ ID NO: 57 + SEQ ID NO: 80 |
| L1007H1000 | SEQ ID NO: 39 + SEQ ID NO: 92 |
| L1008H1000 | SEQ ID NO: 40 + SEQ ID NO: 92 |
| L1009H1000 | SEQ ID NO: 41 + SEQ ID NO: 92 |
| L1010H1000 | SEQ ID NO: 42 + SEQ ID NO: 92 |
| L1011H1000 | SEQ ID NO: 43 + SEQ ID NO: 92 |
| L1012H1000 | SEQ ID NO: 44 + SEQ ID NO: 92 |
| L1012H1007 | SEQ ID NO: 44 + SEQ ID NO: 62 |
| L1012H1016 | SEQ ID NO: 44 + SEQ ID NO: 68 |
| L1012H1020 | SEQ ID NO: 44 + SEQ ID NO: 72 |
| L1012H1027 | SEQ ID NO: 44 + SEQ ID NO: 82 |
| L1012H1029 | SEQ ID NO: 44 + SEQ ID NO: 85 |
| L1012H1031 | SEQ ID NO: 44 + SEQ ID NO: 91 |
| L1013H1000 | SEQ ID NO: 48 + SEQ ID NO: 92 |
| L1014H1000 | SEQ ID NO: 49 + SEQ ID NO: 92 |
| L1015H1000 | SEQ ID NO: 50 + SEQ ID NO: 92 |
| L1016H1000 | SEQ ID NO: 45 + SEQ ID NO: 92 |
| L1017H1000 | SEQ ID NO: 46 + SEQ ID NO: 92 |
| L1018H1000 | SEQ ID NO: 47 + SEQ ID NO: 92 |
| L1019H1000 | SEQ ID NO: 56 + SEQ ID NO: 92 |
| L1020H1000 | SEQ ID NO: 55 + SEQ ID NO: 92 |
| L1020H1007 | SEQ ID NO: 55 + SEQ ID NO: 62 |
| L1020H1016 | SEQ ID NO: 55 + SEQ ID NO: 68 |
| L1020H1020 | SEQ ID NO: 55 + SEQ ID NO: 72 |
| L1020H1027 | SEQ ID NO: 55 + SEQ ID NO: 82 |
| L1020H1029 | SEQ ID NO: 55 + SEQ ID NO: 85 |
| L1020H1031 | SEQ ID NO: 55 + SEQ ID NO: 91 |
| L1021H1000 | SEQ ID NO: 54 + SEQ ID NO: 92 |
| L1021H1007 | SEQ ID NO: 54 + SEQ ID NO: 62 |
| L1021H1016 | SEQ ID NO: 54 + SEQ ID NO: 68 |
| L1021H1020 | SEQ ID NO: 54 + SEQ ID NO: 72 |
| L1021H1027 | SEQ ID NO: 54 + SEQ ID NO: 82 |
| L1021H1029 | SEQ ID NO: 54 + SEQ ID NO: 85 |
| L1021H1031 | SEQ ID NO: 54 + SEQ ID NO: 91 |
| L1022H1000 | SEQ ID NO: 53 + SEQ ID NO: 92 |
| L1023H1000 | SEQ ID NO: 51 + SEQ ID NO: 92 |
| L1024H1000 | SEQ ID NO: 52 + SEQ ID NO: 92 |
| L1024H1007 | SEQ ID NO: 52 + SEQ ID NO: 62 |
| L1024H1031 | SEQ ID NO: 52 + SEQ ID NO: 91 |
| L1001H1000 | SEQ ID NO: 58 + SEQ ID NO: 92 |
| L1000H1001 | SEQ ID NO: 57 + SEQ ID NO: 93 |
| L1012H1001 | SEQ ID NO: 44 + SEQ ID NO: 93 |
| L1001H1031 | SEQ ID NO: 58 + SEQ ID NO: 91 |
| L1020H1001 | SEQ ID NO: 55 + SEQ ID NO: 93 |
| L1023H1001 | SEQ ID NO: 51 + SEQ ID NO: 93 |
| L1000H1000 | SEQ ID NO: 57 + SEQ ID NO: 92 |
| L1001H1001 | SEQ ID NO: 58 + SEQ ID NO: 93 |

Example 1: Preparation of the Antibodies of the Present Invention and Determination of Expression Levels by Non-Reduced SDS-PAGE Gel Electrophoresis The sequence coding for the light chain variable region of the antibody was inserted into vector pFUSE2ss-CLIg-hK (Invivogen, Catalog Number: pfuse2ss-hclk) using EcoRI and BsiWI restriction sites to construct a light chain expression vector. The sequence coding for the heavy chain variable region of the antibody was inserted into vector pFUSEss-CHIg-hG2 (Invivogen, Catalog Number: pfusess-hchg2) or vector pFUSEss-CHIg-hG4 (Invivogen, Catalog Number: pfusess-hchg4) using EcoRI and NheI restriction sites to construct a heavy chain expression vector.

The culture and transfection of Expi293 cells were performed in accordance with the handbook of Expi293™ Expression System Kit from Invitrogen (Catalog Number: A14635). The density of the cells was adjusted to $2\times10^6$ cells/ml for transfection, and 0.6 µg of the light chain expression vector as described above and 0.4 µg of the heavy chain expression vector as described above were added to each ml of cell culture, and the supernatant of the culture was collected four days later.

The culture supernatant was subjected to non-reduced SDS-PAGE gel electrophoresis in accordance with the protocol described in Appendix 8, the Third edition of the "Molecular Cloning: A Laboratory Manual".

Pictures were taken with a gel scanning imaging system from BEIJING JUNYI Electrophoresis Co., LTD and in-gel quantification was performed using Gel-PRO ANALYZER software to determine the expression levels of the antibodies after transient transfection. Results were expressed relative to the expression level of control antibody 1 (control antibody 1 was constructed according to U.S. Pat. No. 7,186,809, which comprises a light chain variable region as set forth in SEQ ID NO: 10 of U.S. Pat. No. 7,186,809 and a heavy chain variable region as set forth in SEQ ID NO: 12 of U.S. Pat. No. 7,186,809, the same below) (control antibody 2 was constructed according to U.S. Pat. No. 7,638,606, which comprises a light chain variable region as set forth in SEQ ID NO: 6 of U.S. Pat. No. 7,638,606 and a variable region as set forth in SEQ ID NO: 42 of U.S. Pat. No. 7,638,606, the same below). See Tables 2a-2c below for the results.

TABLE 2a

Expression levels of the antibodies of the present invention after transient transfection (antibodies whose expression levels are significantly higher than that of control antibody 1):

| Number of the antibody | Expression level vs control antibody 1 | Number of the antibody | Expression level vs control antibody 1 |
|---|---|---|---|
| L1021H1000 | 2.08 | L1000H1028 | 1.27 |
| L1020H1000 | 1.58 | L1000H1015 | 1.19 |
| L1000H1027 | 1.56 | L1000H1032 | 1.18 |
| L1000H1024 | 1.51 | L1000H1026 | 1.15 |
| L1000H1025 | 1.48 | L1021H1029 | 1.12 |
| L1001H1000 | 1.48 | L1000H1030 | 1.1 |
| L1021H1016 | 1.43 | L1024H1031 | 1.08 |
| L1000H1014 | 1.35 | L1000H1016 | 1.05 |

TABLE 2b

Expression levels of the antibodies of the present invention after transient transfection (antibodies whose expression levels are slightly lower than that of control antibody 1):

| Number of the antibody | Expression level vs control antibody 1 | Number of the antibody | Expression level vs control antibody 1 |
|---|---|---|---|
| L1000H1031 | 0.99 | L1017H1000 | 0.85 |
| L1021H1031 | 0.99 | L1020H1016 | 0.84 |
| L1020H1029 | 0.96 | L1000H1009 | 0.81 |
| control antibody 2 | 0.93 | L1000H1007 | 0.8 |
| L1012H1000 | 0.89 | L1000H1023 | 0.8 |
| L1019H1000 | 0.87 | L1020H1027 | 0.78 |
| L1020H1031 | 0.87 | L1024H1007 | 0.77 |
| L1021H1020 | 0.87 | L1000H1013 | 0.75 |
| L1000H1029 | 0.86 | L1020H1007 | 0.74 |
| L1008H1000 | 0.86 | L1021H1007 | 0.74 |
| L1000H1001 | 0.85 | L1000H1021 | 0.71 |

TABLE 2c

Expression levels of the antibodies of the present invention after transient transfection (antibodies whose expression levels are significantly lower than that of control antibody 1):

| Number of the antibody | Expression level vs control antibody 1 | Number of the antibody | Expression level vs control antibody 1 |
|---|---|---|---|
| L1000H1020 | 0.69 | L1024H1000 | 0.52 |
| L1010H1000 | 0.69 | L1000H1008 | 0.51 |
| L1000H1022 | 0.67 | L1000H1037 | 0.5 |
| L1000H1012 | 0.64 | L1007H1000 | 0.49 |
| L1022H1000 | 0.64 | L1016H1000 | 0.49 |
| L1011H1000 | 0.63 | L1000H1017 | 0.47 |
| L1000H1011 | 0.62 | L1000H1035 | 0.46 |
| L1000H1033 | 0.62 | L1012H1027 | 0.46 |
| L1020H1020 | 0.61 | L1018H1000 | 0.44 |
| L1000H1036 | 0.6 | L1023H1000 | 0.43 |
| L1021H1027 | 0.6 | L1012H1016 | 0.42 |
| L1012H1007 | 0.59 | L1013H1000 | 0.41 |
| L1009H1000 | 0.57 | L1000H1034 | 0.4 |
| L1012H1020 | 0.57 | L1000H1018 | 0.35 |
| L1012H1031 | 0.56 | L1000H1019 | 0.34 |
| L1000H1038 | 0.54 | L1015H1000 | 0.27 |
| L1012H1029 | 0.54 | L1014H1000 | 0.17 |
| L1000H1010 | 0.53 | | |

Example 2: Detection of Inhibitory Effect of the Antibodies of the Present Invention on Proliferation of TF-1 Cells by hIL-4 or hIL-13

1. Preparation of Reagents hIL-4 (Invivogen, Catalog Number: rhil-4) solution: hIL-4 was dissolved in 100 μl of PBS containing 0.1% BSA (Beyotime, Catalog Number: ST023) to obtain a solution with a concentration of 100 μg/ml, and the dissolved hIL-4 was dispensed into 1.5 ml (Nunc) centrifuge tubes in a volume of 5 μl per tube, and then the tubes were stored in a refrigerator at −20° C.

WST-1 (Beyotime, Catalog Number: C0036) solution: 5 ml of electron coupling agent (C0036-2) was added to WST-1 powder (C0036-1), and the WST-1 solution was obtained when the WST-1 powder was dissolved completely, then dispensed into 1.5 ml (Nunc) centrifuge tubes in a volume of 620 μl per tube, and then the tubes were stored in a refrigerator at −20° C.

2. Culture of TF-1 Cells

TF-1 cells (ATCC: CRL-2003™) frozen in liquid nitrogen were taken out, shaken in a 37° C. water bath to dissolve quickly. The dissolved cell suspension was transferred to a 15 ml centrifuge tube, and then 1640 medium was added therein to 10 ml. The tube was centrifuged at 800 rpm for 5 min, the supernatant therein was aspirated, and cell pellets were retained and washed once again. 10 ml of 1640 medium containing 10% FBS and 2 ng/ml GM-CSF (Sino Biological, Catalog Number: 10015-H01H) was added to the tube, and a cell density of $1 \times 10^5$-$1 \times 10^6$ cells/ml was obtained. The suspension was transferred to a T75 cell culture flask (Nunc), and the cells were statically cultured in an incubator (Thermo) at 37° C., 5% $CO_2$. Every 2-3 days, the cell suspension was taken out, centrifuged at 800 rpm for 5 min, and the cells were resuspended in 10 ml of medium. Subsequently, $1 \times 10^6$ cells were counted and transferred into a new T75 cell culture flask, and the medium was supplemented thereto to 10 ml. The cells were continuously passaged for 2-3 times to reach a good state (the cells were bright and had a slightly irregular shape when suspended individually) for proliferation blocking experiment.

3. Preparation and Purification of the Antibodies a) Cell Culture Supernatant Samples of the Antibodies of the Present Invention:

Expi293 cells were transfected with plasmids carrying different groups of genes of the antibodies, and 200 μl of the cell culture supernatant was taken out 4 days after transfection, and then centrifuged at 800 rpm for 5 min. The supernatant was filtered through a 0.22 μm pore size filter and used for proliferation blocking experiment.

b) Purified antibody samples of the present invention: For each antibody of the present invention, the culture supernatant of cells expressing the antibody was passed through a 0.22 μm filter and then purified by GE MabSelect Sure (Catalog Number: 11003494) Protein A affinity chromatography column in a purification system GE AKTA purifier 10. The purified antibody was collected and concentrated using Amicon ultrafiltration concentrator (Catalog Number: UFC903096) and then quantified. The antibody was diluted with PBS to 0 to 1 μg/ml for the proliferation blocking experiment.

4. Proliferation Blocking Experiment

The well-grown cells in the T75 cell flask were taken out and transferred into a 15 ml centrifuge tube, which was then centrifuged at 800 rpm for 5 min. The supernatant was discarded and the cell pellets were resuspended with 10 ml PBS, centrifuged at 800 rpm for 5 min. The supernatant was discarded and the cell pellets were resuspended in 10 ml of 1640 medium (without GM-CSF) containing 10% FBS, centrifuged at 800 rpm for 5 min. The supernatant was discarded and the cell pellets were resuspended in 5 ml of 1640 medium (without GM-CSF) containing 10% FBS. The cells were counted and adjusted to a cell density of $5 \times 10^5$ cells/ml through supplementing the medium. The cell suspension was added to a 96-well plate at a volume of 80 μl per well (wells in the outer ring were left free of cells to prevent volatilization). For each antibody of the present invention, 10 μl of purified antibody with different concentrations or 10 μl of the corresponding cell culture supernatant was added to the cells in the 96-well plate (in 3 replicate wells). The hIL-4 was then diluted to 50 ng/ml with 1640 medium containing 10% FBS, and was added to the corresponding wells in the 96-well plate in a volume of 10 μl per well, so that the final cell density was $4 \times 10^5$ cells/ml, the concentration of hIL-4 was 5 ng/ml, and the volume in each well of the 96-well plate was 100 μl. A negative control group (in 3 replicate wells) was set, in which no hIL-4 or the antibody was added, and only the same number of cells and the same volume of the culture medium were added. Meanwhile, a positive control group (in 3 replicate wells) with addition of the same concentration of hIL-4 and the same volume of the medium was set, and no antibody was added in in this group. 200 μl of PBS was added to each well in the outer ring of the 96-well cell plate to prevent the volatilization of liquid in the inner ring. The 96-well cell plate was placed in a 5% $CO_2$ incubator at 37° C. for static culture.

The above experiment was repeated with the same procedure using 500 ng/ml of hIL-13 (its final concentration was 50 ng/ml after being added into the cells).

5. Data Statistics

After the 96-well cell plates were statically cultured for 72 hours in the 5% $CO_2$ incubator, 10 μl of the WST-1 solution was added to the cells in each well. The 96-well cell plate was placed in a 5% CO2 incubator at 37° C. for further static culture. 24 h later, the 96-well plate was placed in flexstation 3 (Molecular Devices) and the values of OD450-OD650 were read.

For the culture supernatants of the antibodies of the invention, the values of OD450-OD650 (OD value) of them and those of the positive control group and the negative control group were used to calculate inhibitory rate as follows: inhibitory rate=(OD value of supernatant of the transfected cells−OD value of the positive control group)/(OD value of the negative control group−OD value of the positive control group)×100%. The results of blocking effect of the antibodies of the present invention on the proliferation of TF-1 cells by hIL-4 or hIL-13 are shown in Tables 3a-3b below.

For the purified antibodies of the present invention with different concentrations, the measured OD450-OD650 data were input into prism5 software, in which the value of the negative control group was set to the lowest one, the value of the positive control group was set to the highest one, and the logarithm of the antibody concentration was taken. Then the curve of the antibody concentration logarithm to the OD450-OD650 value was fitted by prism5 software. The calculated IC50s are shown in Table 4 below.

TABLE 3a

Screening results of inhibitory effects of the antibodies of the present invention on the proliferation activity of TF-1 cells (antibodies with increased inhibitory rates compared with control antibody 1).

| Number of the antibody | Inhibitory rate on pro-proliferative effect of IL-4 | Inhibitory rate on pro-proliferative effect of IL-13 |
|---|---|---|
| control antibody 1 | 0.87 | 0.63 |
| control antibody 2 | 1 | 0.87 |
| L1020H1029 | 1.03 | 0.93 |
| L1000H1001 | 1.03 | 0.93 |
| L1021H1027 | 1.02 | 0.94 |
| L1020H1027 | 1.02 | 0.92 |
| L1021H1029 | 1.02 | 0.92 |
| L1020H1016 | 1.01 | 0.97 |
| L1024H1031 | 1.01 | 0.94 |
| L1021H1031 | 1.01 | 0.93 |
| L1020H1031 | 1.01 | 0.93 |
| L1000H1029 | 1.01 | 0.92 |
| L1000H1027 | 1.01 | 0.86 |
| L1021H1016 | 1 | 0.94 |
| L1021H1007 | 1 | 0.86 |
| L1000H1028 | 1 | 0.84 |
| L1000H1014 | 0.99 | 0.78 |
| L1001H1000 | 0.98 | 0.85 |
| L1000H1024 | 0.98 | 0.75 |
| L1000H1031 | 0.97 | 0.83 |
| L1000H1007 | 0.96 | 0.82 |
| L1000H1023 | 0.96 | 0.8 |
| L1000H1032 | 0.96 | 0.74 |
| L1020H1007 | 0.95 | 0.9 |
| L1021H1000 | 0.95 | 0.78 |
| L1000H1016 | 0.95 | 0.76 |
| L1012H1029 | 0.94 | 0.95 |
| L1012H1007 | 0.93 | 0.88 |
| L1021H1020 | 0.91 | 0.75 |
| L1020H1000 | 0.91 | 0.7 |
| L1000H1025 | 0.91 | 0.69 |
| L1012H1020 | 0.9 | 0.78 |
| L1000H1020 | 0.88 | 0.76 |
| L1000H1012 | 0.88 | 0.58 |
| L1020H1020 | 0.87 | 0.76 |

TABLE 3b

Screening results of inhibitory effects of the antibodies of the present invention on the proliferation activity of TF-1 cells (antibodies with the same or decreased inhibitory rates compared with control antibody 1).

| Number of the antibody | Inhibitory rate on pro-proliferative effect of IL-4 | Inhibitory rate on pro-proliferative effect of IL-13 |
|---|---|---|
| L1000H1022 | 0.87 | 0.62 |
| L1000H1017 | 0.87 | 0.59 |
| L1000H1030 | 0.87 | 0.47 |
| L1024H1007 | 0.86 | 0.7 |
| L1000H1013 | 0.86 | 0.55 |
| L1012H1031 | 0.85 | 0.7 |
| L1000H1015 | 0.85 | 0.63 |
| L1000H1026 | 0.85 | 0.53 |
| L1000H1018 | 0.84 | 0.65 |
| L1000H1009 | 0.83 | 0.54 |
| L1012H1000 | 0.78 | 0.5 |
| L1012H1016 | 0.78 | 0.48 |
| L1000H1021 | 0.73 | 0.56 |
| L1019H1000 | 0.72 | 0.49 |
| L1008H1000 | 0.67 | 0.27 |
| L1009H1000 | 0.66 | 0.35 |
| L1000H1008 | 0.66 | 0.19 |
| L1012H1027 | 0.65 | 0.63 |
| L1000H1011 | 0.61 | 0.26 |
| L1000H1010 | 0.54 | 0.1 |
| L1000H1019 | 0.52 | 0.29 |
| L1007H1000 | 0.49 | 0.15 |
| L1024H1000 | 0.44 | 0.39 |
| L1011H1000 | 0.44 | 0.13 |
| L1017H1000 | 0.44 | 0.02 |
| L1018H1000 | 0.42 | −0.12 |
| L1010H1000 | 0.38 | 0.06 |
| L1000H1036 | 0.27 | 0.18 |
| L1023H1000 | 0.26 | 0.07 |
| L1000H1033 | 0.23 | 0.14 |
| L1015H1000 | 0.16 | 0.09 |
| L1000H1034 | 0.15 | 0.1 |
| L1016H1000 | 0.1 | −0.36 |
| L1013H1000 | 0.01 | −0.21 |
| L1022H1000 | −0.05 | 0.02 |
| L1000H1038 | −0.05 | −0.15 |
| L1014H1000 | −0.05 | −0.29 |
| L1000H1037 | −0.06 | −0.13 |
| L1000H1035 | −0.12 | −0.13 |

TABLE 4

Activity data of the purified antibodies
(600-900 ml) after transient transfection

|  | IC50 (ng/ml) (Inhibition on the proliferation of IL-4) | IC50 (ng/ml) (Inhibition on the proliferation of IL-13) |
|---|---|---|
| control antibody 1 | 184.03 ± 61.95 | 345.1 ± 73.9 |
| control antibody 2 | 27.79 ± 3.22 | 52.06 ± 14.97 |
| L1021H1016 | 28.46 ± 7.82 | 69.67 ± 28.38 |
| L1021H1020 | 15.36 ± 2.46 | 28.64 ± 10.46 |
| L1021H1031 | 34.27 ± 12.17 | 76.51 ± 31.94 |
| L1020H1016 | 24.19 ± 6.91 | 44.62 ± 14.79 |
| L1020H1020 | 23.63 ± 8.73 | 53.73 ± 17.34 |
| L1020H1031 | 25.6 ± 7.46 | 60.17 ± 19.02 |
| L1012H1016 | 32.44 ± 7.45 | 75.33 ± 43.63 |
| L1012H1020 | 21.09 ± 4.72 | 56.65 ± 23.34 |
| L1012H1031 | 39.26 ± 15.61 | 76.87 ± 40.97 |

Example 3 Detection of the Binding Abilities of the Antibodies of the Present Invention to sIL-4Rα by ELISA 1. Preparation of Reagents sIL-4Rα (PEPRO TECH, Catalog Number: 200-04R) solution: the sIL-4Rα was taken and 1 ml ddH2O was added therein, mixed up and down, and then a solution of 100 µg/ml was obtained. The solution was stored in a refrigerator at −20° C. after being subpacked.

Sample to be tested: For each antibody of the present invention, 10 µl and 2 µl of the culture supernatant of Expi293 cells expressing the antibody after transient transfection (the medium was Expi293 Expression Medium, Invitrogen, Catalog Number: A1435102; suspension culture was performed for 4 days at 100 rpm in a 8% CO2 incubator) were respectively added to 990 µl and 998 µl of PBS to prepare antibody samples to be tested of 1:100 and 1:500 dilutions.

Control sample: As negative control samples, the culture supernatant of normal cells (untransfected Expi293 cells; the medium was Expi293 Expression Medium, Invitrogen, Catalog Number: A1435102; suspension culture was performed for 4 days at 100 rpm in a 8% CO2 incubator) were also diluted at 1:100 and 1:500.

2. Detection by ELISA

100 µl of 100 µg/ml sIL-4Rα solution was added to 9.90 ml of PBS, mixed up and down, and then an antigen coating buffer of 1.0 µg/ml was obtained. The prepared antigen coating buffer was added to a 96-well ELISA plate (Corning) with a volume of 100 µl per well. The 96-well ELISA plate was incubated overnight in a refrigerator at 4° C. On the next day, the solution therein was discarded, and PBS containing 2% BSA was added to the 96-well ELISA plate row by row with a volume of 300 µl per well. The 96-well ELISA plate was incubated for 2 hours in a refrigerator at 4° C. Then the PBS containing 2% BSA was discarded and the plate was washed 3 times with PBST. Diluted antibodies to be tested were sequentially added to the corresponding wells, while the normal cell culture supernatants, as negative control samples, were added too. Three duplicate wells were made for each sample with a volume of 100 µl per well. The ELISA plate was wrapped with preservative film (or covered) and incubated for 1 h at 10° C. in a constant temperature incubator. Subsequently, the 96-well ELISA plate was taken out, and the solution therein was discarded. After washing with PBST for 3 times, TMB solution (Solarbio, Catalog Number: PR1200) was added to the 96-well ELISA plate row by row with a volume of 100 µl per well. The 96-well ELISA plate was placed at room temperature for 5 minutes, and 2 M H2SO4 solution was added in immediately to terminate the reaction. The 96-well ELISA plate was placed in flexstation 3 (Molecular Devices), the values of OD450 were read, and the data were collected, calculated and analyzed. Results were expressed relative to the affinity of control antibody 1. See Tables 5a-5c below for the results.

TABLE 5a

The affinities of the antibodies of the present invention for sIL-4Rα (antibodies whose affinities are significantly greater than that of control antibody 1)

| Number of the antibody | OD 450/ OD450$_{Control\ antibody\ 1}$ |
|---|---|
| Control antibody 1 | 1 |
| L1021H1000 | 2.42 |
| L1020H1000 | 2.27 |
| L1019H1000 | 1.79 |
| L1001H1000 | 1.56 |
| L1012H1000 | 1.22 |
| L1000H1031 | 1.14 |
| L1020H1031 | 1.12 |
| L1000H1014 | 1.06 |
| L1020H1029 | 1.01 |

TABLE 5b

The affinities of the antibodies of the present invention for sIL-4Rα (antibodies whose affinities are equal to or slightly lower than that of control antibody 1)

| Number of the antibody | OD 450/ OD450$_{Control\ antibody\ 1}$ |
|---|---|
| L1010H1000 | 1 |
| L1021H1029 | 1 |
| L1011H1000 | 0.9 |
| L1008H1000 | 0.9 |
| L1021H1031 | 0.9 |
| L1024H1031 | 0.9 |
| L1007H1000 | 0.8 |
| L1020H1016 | 0.8 |
| L1000H1029 | 0.8 |
| L1000H1001 | 0.7 |

TABLE 5c

The affinities of the antibodies of the present invention for sIL-4Rα (antibodies whose affinities significantly lower than that of control antibody 1)

| Number of the antibody | OD 450/ OD450$_{Control\ antibody\ 1}$ |
|---|---|
| L1024H1000 | 0.69 |
| L1015H1000 | 0.67 |
| L1000H1015 | 0.65 |
| L1009H1000 | 0.64 |
| L1021H1016 | 0.63 |
| L1000H1023 | 0.63 |
| L1000H1016 | 0.61 |
| L1000H1009 | 0.56 |
| L1000H1032 | 0.53 |
| L1017H1000 | 0.49 |
| L1021H1007 | 0.44 |
| L1000H1027 | 0.44 |
| L1020H1007 | 0.40 |
| L1020H1027 | 0.40 |
| L1012H1007 | 0.40 |
| L1000H1013 | 0.38 |
| L1000H1007 | 0.37 |

TABLE 5c-continued

The affinities of the antibodies of the present invention for sIL-4Rα (antibodies whose affinities significantly lower than that of control antibody 1)

| Number of the antibody | OD 450/ OD450$_{Control\ antibody\ 1}$ |
|---|---|
| L1000H1021 | 0.35 |
| L1000H1028 | 0.33 |
| L1021H1027 | 0.29 |
| L1016H1000 | 0.27 |
| L1020H1020 | 0.26 |
| L1000H1024 | 0.26 |
| L1021H1020 | 0.24 |
| L1013H1000 | 0.24 |
| L1024H1007 | 0.23 |
| L1000H1020 | 0.23 |
| L1000H1035 | 0.22 |
| L1000H1008 | 0.21 |
| L1000H1025 | 0.21 |
| L1000H1030 | 0.20 |
| L1000H1012 | 0.18 |
| L1000H1022 | 0.18 |
| L1022H1000 | 0.16 |
| L1012H1031 | 0.16 |
| L1000H1017 | 0.13 |
| L1000H1010 | 0.11 |
| L1000H1026 | 0.11 |
| L1012H1020 | 0.11 |
| L1012H1029 | 0.11 |
| L1000H1036 | 0.10 |
| L1000H1018 | 0.09 |
| L1000H1034 | 0.09 |
| L1000H1011 | 0.09 |
| L1000H1033 | 0.08 |
| L1012H1016 | 0.08 |
| L1018H1000 | 0.06 |
| L1023H1000 | 0.05 |
| L1000H1038 | 0.04 |
| L1000H1019 | 0.02 |
| L1012H1027 | 0.02 |
| L1014H1000 | 0.01 |
| L1000H1037 | −0.01 |

Example 4: Pharmacokinetics of the Antibodies of the Present Invention in Mouse a Series of Pharmacokinetic Experiments were Carried Out in Mice to Further Screen Antibodies 6-8 week-old SPF Balb/c mice were selected and injected subcutaneously with antibodies (the antibodies of the present invention or control antibody 2) in a dose of 5 mg/kg (weight of the mouse). Blood samples were collected at the time points before administration (0 h) and at 2, 8, 24, 48, 72, 120, 168, 216, 264, 336 h after administration. For blood sampling, the animals were anesthetized by inhaling isoflurane, blood samples were taken from the orbital venous plexus, and the sampling volume for each animal was about 0.1 ml; 336 h after administration, the animals were anesthetized by inhaling isoflurane and then euthanized after taking blood in the inferior vena cava.

No anticoagulant was added to the blood samples, and serum was isolated from each sample by centrifugation at 1500 g for 10 min at room temperature within 2 h after blood sampling. The collected supernatants were immediately transferred to new labeled centrifuge tubes and then stored at −70° C. for temporary storage. The concentrations of the antibodies in the mice were determined by ELISA:

1. Preparation of Reagents sIL-4Rα (PEPRO TECH, Catalog Number: 200-04R) solution: sIL-4Rα was taken and 1 ml ddH2O was added therein, mixed up and down, and then a solution of 100 μg/ml was obtained. The solution was stored in a refrigerator at −20° C. after being subpacked.

Sample to be tested: 1 μl of serum collected at different time points was added to 999 μl of PBS containing 1% BSA to prepare a serum sample to be tested of 1:1000 dilution.

Standard sample: The antibody to be tested was diluted to 0.1 μg/ml with PBS containing 1% BSA and 0.1% normal animal serum (Beyotime, Catalog Number: ST023). Afterwards, 200, 400, 600, 800, 900, 950, 990 and 1000 μl of PBS containing 1% BSA and 0.1% normal animal serum were respectively added to 800, 600, 400, 200, 100, 50, 10 and 0 μl of 0.1 μg/ml antibodies to be tested, and thus standard samples of the antibodies of the present invention were prepared with a final concentration of 80, 60, 40, 20, 10, 5, 1, or 0 ng/ml respectively.

2. Detection by ELISA

250 μl of 100 μg/ml sIL-4Rα solution was added to 9.75 ml of PBS, mixed up and down, and then an antigen coating buffer of 2.5 μg/ml was obtained. The prepared antigen coating buffer was added to a 96-well ELISA plate (Corning) with a volume of 100 μl per well. The 96-well ELISA plate was incubated overnight in a refrigerator at 4° C. after being wrapped with preservative film (or covered). On the next day, the 96-well ELISA plate was taken out and the solution therein was discarded, and PBS containing 2% BSA was added thereto with a volume of 300 μl per well. The 96-well ELISA plate was incubated for 2 hours in a refrigerator at 4° C. after being wrapped with preservative film (or covered). Then the 96-well ELISA plate was taken out and the solution therein was discarded, and the plate was washed 3 times with PBST. The diluted standard antibodies and the sera to be detected were sequentially added to the corresponding wells, and three duplicate wells were made for each sample with a volume of 100 μl per well. The ELISA plate was wrapped with preservative film (or covered) and incubated for 1 h at room temperature. Subsequently, the solution in the 96-well ELISA plate was discarded and then the plate was washed with PBST for 3 times. Later, TMB solution (Solarbio, Catalog Number: PR1200) was added to the 96-well ELISA plate row by row with a volume of 100 μl per well. The 96-well ELISA plate was placed at room temperature for 5 minutes, and 2 M H2SO4 solution was added in immediately to terminate the reaction. The 96-well ELISA plate was then placed in flexstation 3 (Molecular Devices), the values of OD450 were read, the data were collected and the results were calculated with Winnonlin software. The pharmacokinetic results were shown in FIG. 1 and Table 6 below.

TABLE 6

Pharmacokinetic results of the antibodies of the present invention in mouse

| Number | | Half life h | Time to peak h | Peak concentration μg/ml | Area Under the drug-time Curve h*μg/ml | Volume of distribution ml/kg | Clearance rate ml/h/kg |
|---|---|---|---|---|---|---|---|
| L1020H1031 | Mean value | 269.34 | 72 | 33.79 | 7679.28 | 138.92 | 0.38 |
| | Standard deviation | 105.73 | 0.00 | 0.42 | 163.91 | 22.48 | 0.09 |
| L1012H1031 | Mean value | 167.27 | 48 | 45.5 | 9852.3 | 91.3 | 0.38 |
| | Standard deviation | 8.52 | 0.00 | 1.86 | 448.34 | 5.58 | 0.00 |
| Control antibody 2 | Mean value | 56.67 | 36 | 7.88 | 1132.68 | 288.92 | 3.79 |
| | Standard deviation | 25.84 | 16.97 | 0.25 | 94.42 | 49.45 | 1.12 |

Example 5: Pharmacokinetics of the Antibodies of the Present Invention in *Macaca fascicularis*

A series of pharmacokinetic experiments were carried out in *Macaca fascicularises* to further screen antibodies.

3-5 year-old *Macaca fascicularises* each weighting 2-5 Kg were selected and injected subcutaneously with antibodies (the antibodies of the present invention or control antibody 2) in a dose of 5 mg/kg (weight of the *Macaca fascicularis*). The antibody or control antibody 2 to be administered was accurately extracted with a disposable aseptic injector, and multi-point injections were made subcutaneously on the inner side of the thigh of the animal, and the injection volume per point was not more than 2 ml. Whole blood samples were collected from the subcutaneous vein of the hind limb of the animal at the time points before administration (0 h) and at 0.5, 2, 4, 8, 24, 48, 72, 120, 168, 240, 336 h, 432 h, 504 h, 600 h, 672 h after administration. The blood volume collected from each animal was about 0.1 ml each time.

Figure 2:
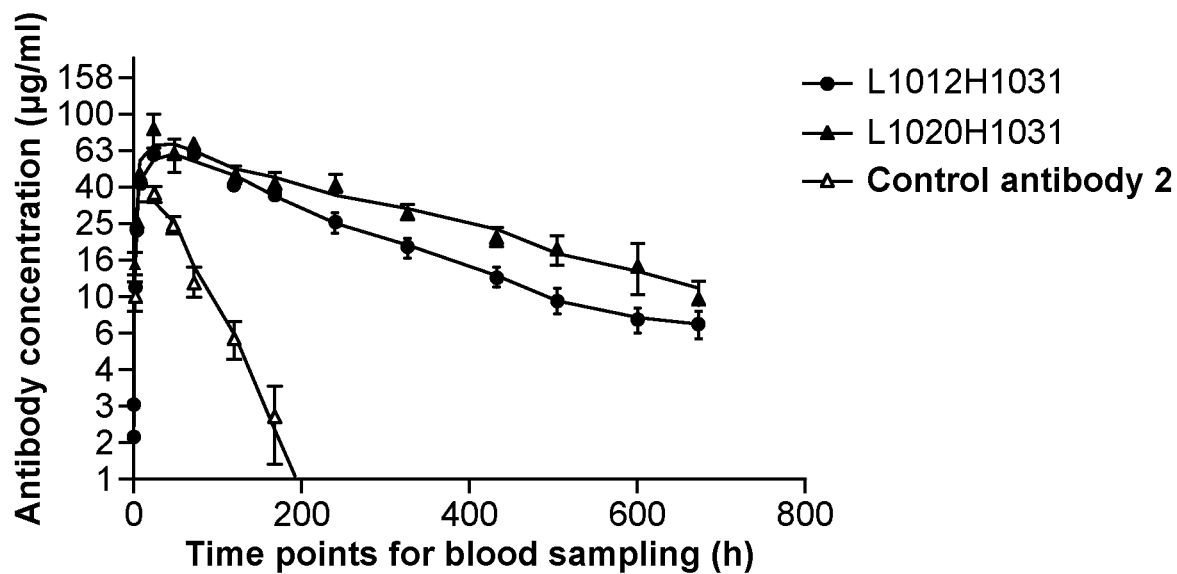
FIG. 2 shows the pharmacokinetic curves of the antibodies of the present invention in *Macaca fascicularis*.

No anticoagulant was added to the blood samples, and serum was isolated from each sample by centrifugation at 1500 g for 10 min at room temperature within 2 h after blood sampling. The collected supernatants were immediately transferred to new labeled centrifuge tubes and then stored at −70° C. for temporary storage. The concentrations of the antibodies in the *Macaca fascicularises* were determined according the method as described in Example 4. The pharmacokinetic results are shown in FIG. 2 and Table 7 below.

TABLE 7

Pharmacokinetic results of the antibodies of the present invention in macaca fascicularis

| Number | | Half life h | Time to peak h | Peak concentration μg/ml | Area Under the drug-time Curve h*μg/ml | Volume of distribution ml/kg | Clearance rate ml/h/kg |
|---|---|---|---|---|---|---|---|
| L1020H1031 | Mean value | 254.95 | 48.00 | 89.65 | 22189.91 | 75.94 | 0.22 |
| | Standard deviation | 44.57 | 33.94 | 44.29 | 8557.15 | 22.95 | 0.10 |
| L1012H1031 | Mean value | 185.75 | 48 | 65 | 16185.73 | 73.41 | 0.28 |
| | Standard deviation | 42.54 | 33.94 | 4.5 | 2506.98 | 0.81 | 0.06 |
| Control antibody 2 | Mean value | 37.03 | 16 | 37.82 | 2773.21 | 93.97 | 1.78 |
| | Standard deviation | 18.03 | 11.31 | 6.75 | 155.84 | 42.47 | 0.07 |

Example 6: Detection of Binding of the Antibodies of the Present Invention to TF-1 Cells by FACS 1. Cell Culture TF-1 cells (ATCC: CRL-2003™) frozen in liquid nitrogen were taken out, shaken in a 37° C. water bath gently to dissolve quickly. The dissolved cell suspension was transferred to a 15 ml centrifuge tube, and then 1640 medium (Hyclone, Catalog Number: SH30809.01B) was added therein to 10 ml. The tube was centrifuged at 800 rpm for 5 min, the supernatant therein was aspirated off, and the cell pellets were retained and washed once again. The cell density was adjusted to $1 \times 10^5$-$1 \times 10^6$ cells/ml with 1640 medium containing 10% FBS (Hyclone, Catalog Number: SV30184.02) and 2 ng/ml GM-CSF (Sino Biological, Catalog Number: 10015-H01H). The suspension was transferred to a T75 cell culture flask (Nunc), and the cells were statically cultured in an incubator (Thermo) at 37° C., 5% $CO_2$. Every 2-3 days, the cell suspension was taken out, centrifuged at 800 rpm for 5 min, and the cells were resuspended in 10 ml of medium. Subsequently, 1×10⁶ cells were counted and transferred into a new T75 cell culture flask, and the medium was supplemented thereto to 10 ml. The cells were continuously passaged for 2-3 times to reach a good state (the cells were bright, and had a slightly irregular shape when suspended individually) for experiment.

2. Cell Treatment

Tf-1 cells were taken and counted under a microscope. The cells were divided into three groups and placed into three 1.5 ml centrifuge tubes respectively. The number of cells for each group was 1×10⁶. The cells were centrifuged at 800 rpm for 5 min, and then resuspended in 1 ml of cold PBS containing 1% BSA for washing once again. Subsequently, the cells were centrifuged at 800 rpm for 5 min, and 45 μl of cold PBS containing 1% BSA was added to each centrifuge tube to resuspend the cells, and then 5 μl (500 μg/ml) of the present antibody L1021H1031, L1020H1031 or L1012H1031 was added to the first centrifuge tube, and 5 μl of PBS was added to the second centrifuge tube as a negative control. The cells were allowed to stand on ice for 45 min and then centrifuged at 800 rpm for 5 min. Afterwards, the cells were resuspended in 1 ml of cold PBS containing 1% BSA for washing once again, and centrifuged at 800 rpm for 5 min. 499 μl of cold PBS containing 1% BSA was added to each centrifuge tube to resuspend the cells, and then 1 μl of FITC-labeled goat anti-human IgG (H+L) (Beyotime, Catalog Number: A0556) was added thereto. After standing on ice for 45 min, the cells were centrifuged at 800 rpm for 5 min, and resuspended in 1 ml of cold PBS containing 1% BSA for washing once again. Thus, the cells to be detected were obtained.

3. Detection by FACS

Figure 3A:
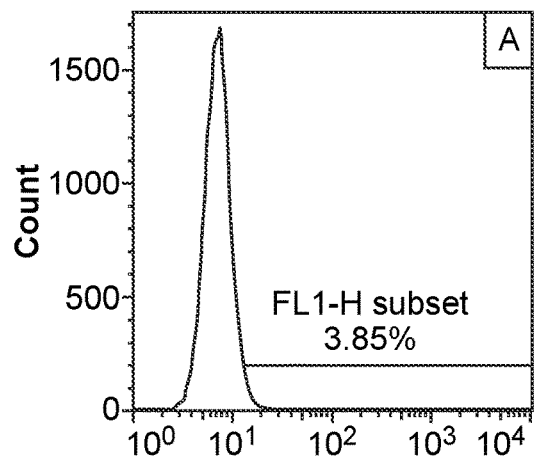
FIG. 3 includes panels 3A-3C which show the specific binding of the antibodies of the present invention with TF-1 cells expressing IL-4Rα, as determined by FACS, in which panel 3A shows the fluorescence signal without the addition of antibody L1012H1031 of the present invention; panel 3B shows the fluorescence signal with the addition of antibody L1012H1031 of the present invention; and panel 3C shows the signal superposition of panels 3A and 3B for comparison.
Figure 3B:
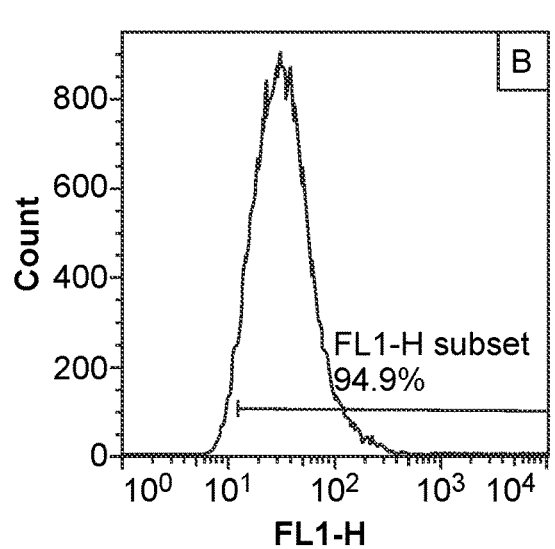
Figure 3C:
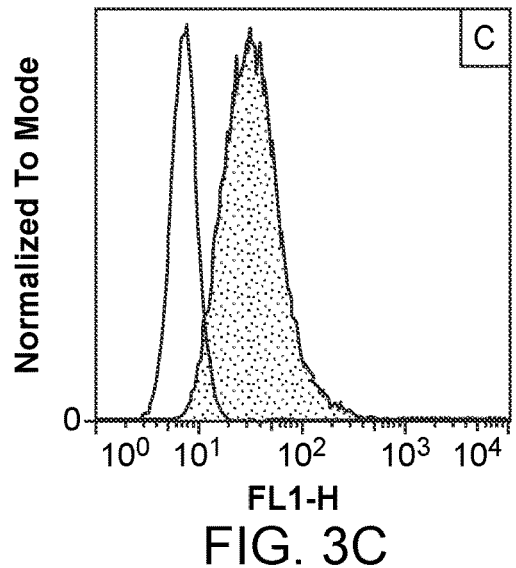
Figure 4A:
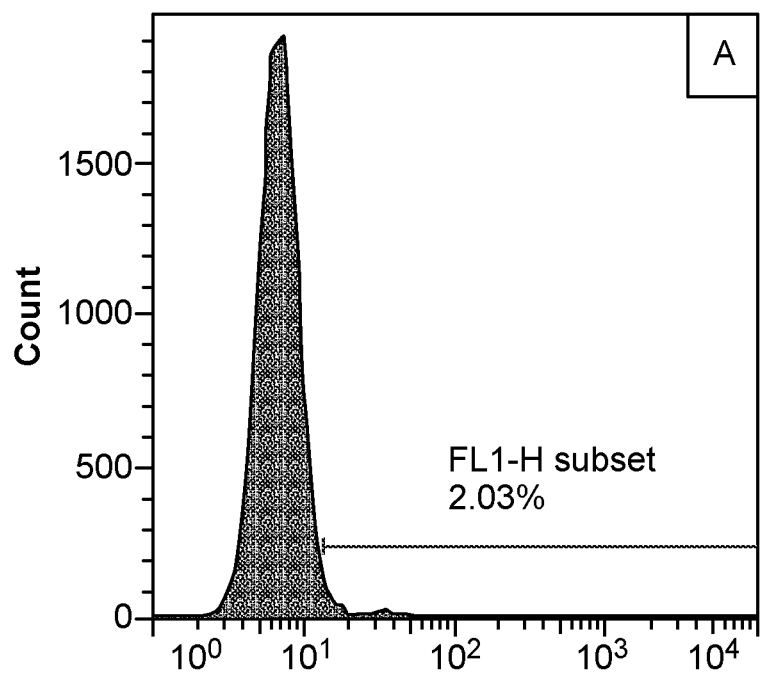
FIG. 4 includes panels 4A-4D which show that the specific binding of the antibodies of the present invention with TF-1 cells expressing IL-4Rα is blocked by sIL-4Rα present in the system, as determined by FACS, in which panel 4A shows the fluorescence signal without the addition of antibody L1012H1031 of the present invention; panel 4B shows the fluorescence signal with the addition of antibody L1012H1031 of the present invention; panel 4C shows the fluorescence signal with the addition of antibody L1012H1031 of the present invention and sIL-4Rα, and panel 4D shows the signal superposition of panels 4A-4C for comparison.
Figure 4B:
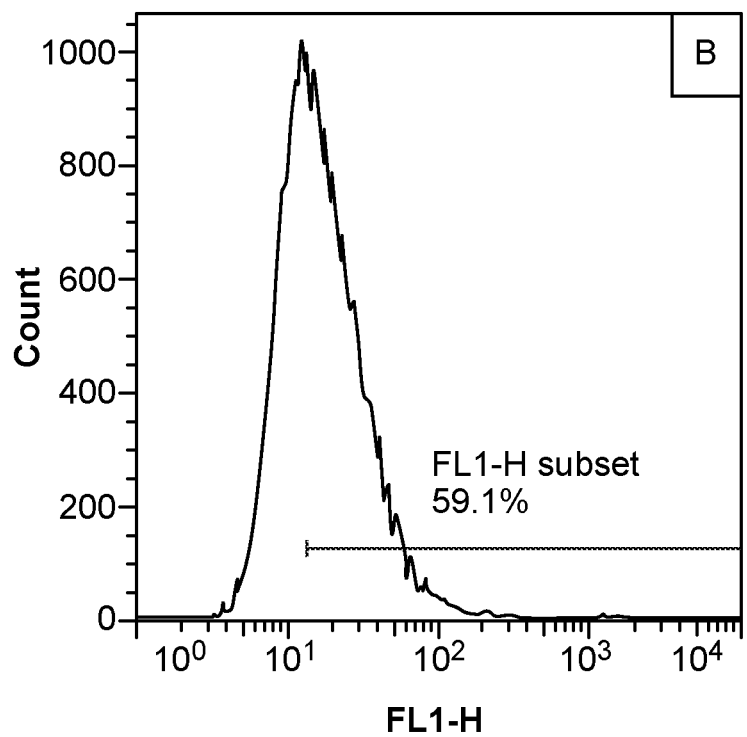
Figure 4C:
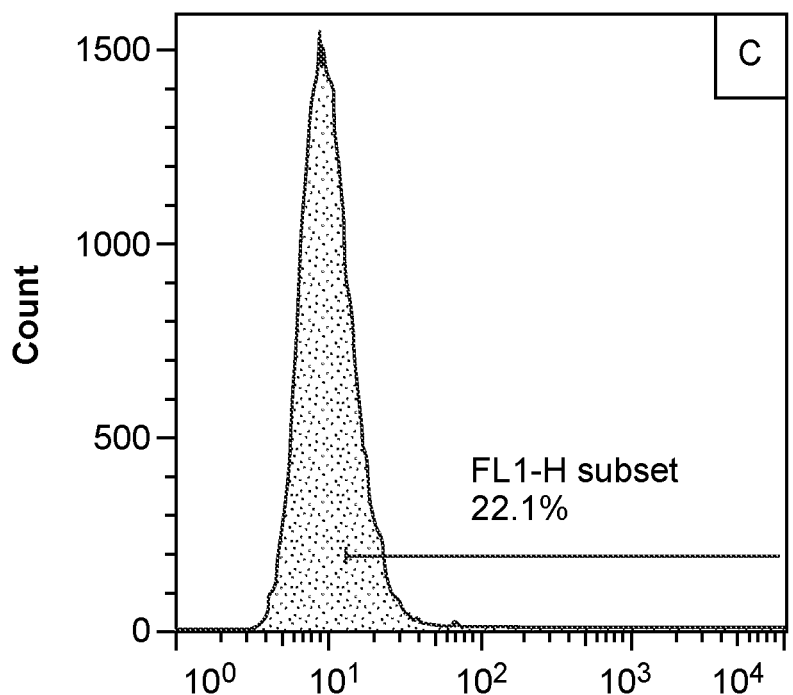
Figure 4D:
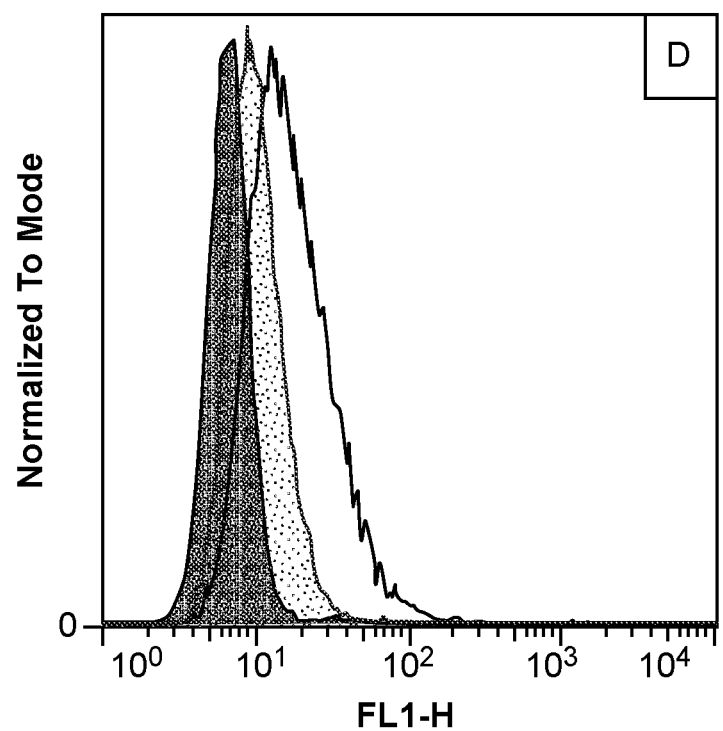

FACS instrument and its operating system were run according to correct protocol. After correct parameters were set, the cells were added into the detection tube to detect fluorescence signal of FL1 channel. The results were analyzed with FlowJo 7.6 software and are shown in FIG. 3, panels 3A-3C. It can be seen that the antibodies of the present invention are capable of specifically binding to TF-1 cells expressing IL-4Rα.

Example 7: Detection of the Blocking Effect of Soluble hIL-4 Rα (sIL-4Rα) on Binding of Antibodies to TF-1 Cells by FACS 1. Preparation of Reagents The hIL-4 (Invivogen, Catalog Number: rhil-4) solution was prepared as described in Example 2.

2. Cell Culture

The TF-1 cells (ATCC: CRL-2003™) were cultured as described in Example 6.

3. Mixing of sIL-4Rα with the Antibodies of the Present Invention

10 μl (100 μg/ml) of sIL-4Rα and 5 μl (500 μg/ml) of antibody L1021H1031, L1020H1031 or L1012H1031 of the present invention were uniformly mixed in a 1.5 ml centrifuge tube at a molar ratio of 2:1. The mixture of 10 μl PBS and 5 μl of antibody L1021H1031, L1020H1031 or L1012H1031 of the present invention was served as a positive control and 15 μl PBS was served as a negative control. The centrifuge tubes were placed in a 37° C. incubator for 1 h. 4. Cell treatment TF-1 cells were taken and then counted under a microscope. The cells were divided into four groups and placed into four 1.5 ml centrifuge tubes respectively. The number of cells for each group was 1×10⁶. The cells were centrifuged at 800 rpm for 5 min, and then resuspended in 1 ml of cold PBS containing 1% BSA for washing once again. Subsequently, the cells were centrifuged at 800 rpm for 5 min, and 35 μl of cold PBS containing 1% BSA was added to each centrifuge tube to resuspend the cells, and then 15 μl of each of different antibody mixtures and the control prepared in step 3 was added to the tubes respectively. After standing on ice for 45 min, the cells were centrifuged at 800 rpm for 5 min, and resuspended in 1 ml of cold PBS containing 1% BSA for washing once again, and centrifuged at 800 rpm for 5 min. 499 μl of cold PBS containing 1% BSA was added to each centrifuge tube to resuspend the cells, and then 1 μl of FITC-labeled goat anti-human IgG (H+L) (Beyotime, Catalog Number: A0556) was added thereto. After standing on ice for 45 min, the cells were centrifuged at 800 rpm for 5 min, and resuspended in 1 ml of cold PBS containing 1% BSA for washing once again. Thus, the cells to be detected were obtained.

5. Detection by FACS

FACS instrument and its operating system were run according to correct protocol. After correct parameters were set, the cells were added into the detection tube to detect fluorescence signal of FL1 channel. The results were analyzed with FlowJo 7.6 software and are shown in FIG. 4, panels 4A-4D. It can be seen that sIL-4Rα can specifically and effectively block the specific binding of the antibodies of the present invention to TF-1 cells.

Example 8: Determination of Antibody Affinity by Bicore

An anti-human Fc (AHC) antibody (GE Healthcare) was coupled to a CM5 chip, and then the antibody of the present invention was captured by AHC respectively. Subsequently, different concentrations of human sIL-4Rα were flowed through the surface of the chip on which the antibody of the present invention was captured. For capture and binding, the present antibody was diluted to 2 μg/ml and the antigen sIL-4Rα was diluted to 0.39, 0.78, 1.56, 3.13, 6.25, 12.5, 25.0, 50.0 and 100.0 nM. The experimental method was then established in the Biacore T200 control software, after which the experimental program was run for detection. The results are shown in Table 8 below.

TABLE 8

Detection results of the antibody affinity

| Number | Ka ($\times 10^5$ M$^{-1}$s$^{-1}$) | Kd ($\times 10^{-5}$ s$^{-1}$) | KD ($10^{-10}$ M) |
|---|---|---|---|
| Control antibody 1 | 7.63 | 52.3 | 6.85 |
| Control antibody 2 | 3.85 | 1.73 | 0.448 |
| L1020H1031 | 4.61 | 4.79 | 1.04 |
| L1012H1031 | 5.18 | 9.49 | 1.83 |

Example 9: Investigation of the Inhibitory Effect of the Antibodies of the Present Invention on TARC and MDC Release by ELISA 10 ml of fresh blood (donated) anticoagulated with heparin was mixed with PBS at room temperature in a ratio of 1:1, and then the mixture was carefully added to 20 ml of human lymphocyte separation solution (Solarbio, Catalog Number: P8610) prepared in advance. After centrifuging at 1500 rpm for 30 min at room temperature, the PBMC layer was carefully aspirated and washed twice with PBS. The cells were finally diluted with 1640 medium containing 10% FBS and 200 IU/ml IL-2, and then added to a 24-well plate with 1×10⁶ cells per well. Afterwards, antibody L1020H1031 with a final concentration of 1000, 300, 100, 30 or 10 ng/ml was added to each well, following by the addition of IL-4 with a final concentration of 10 ng/ml (or IL-13 with a final concentration of 100 ng/ml) thereto. Detection was carried out according to the method provided with Human TARC ELISA kit (Abcam, Catalog Number: ab183366) or Human MDC ELISA kit (Abcam, Catalog Number: ab179885) after 72 hours of culture.

Figure 5A:
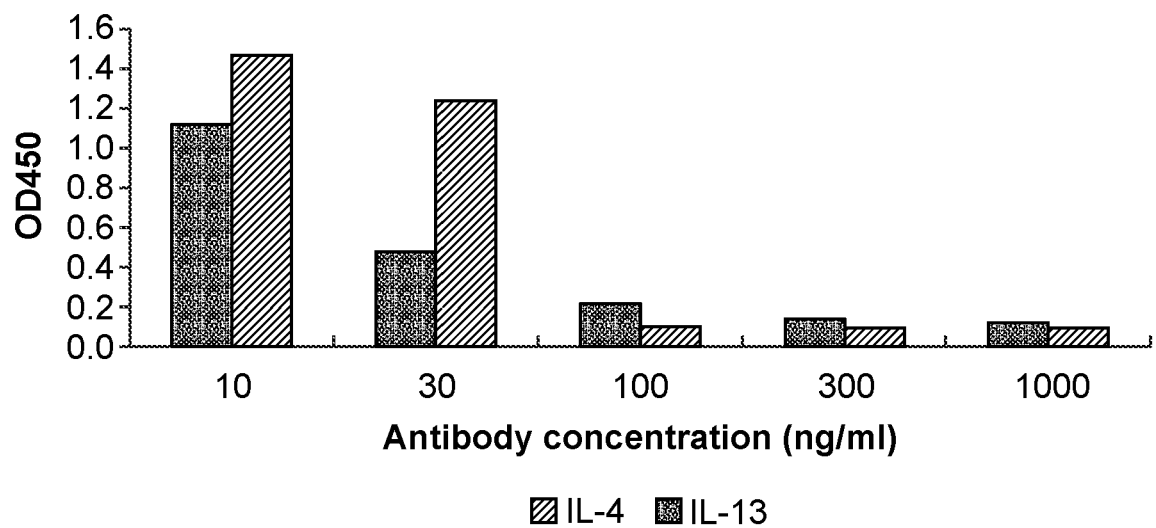
FIG. 5 includes panels 5A-5B which show the effect of the antibodies of the present invention on the inhibition of TARO and MDC release, as determined by ELISA, in which panel 5A shows the result that antibody L1020H1031 of the present invention inhibits TARO release, and panel 5B shows the result that antibody L1020H1031 of the present invention inhibits MDC release.
Figure 5B:
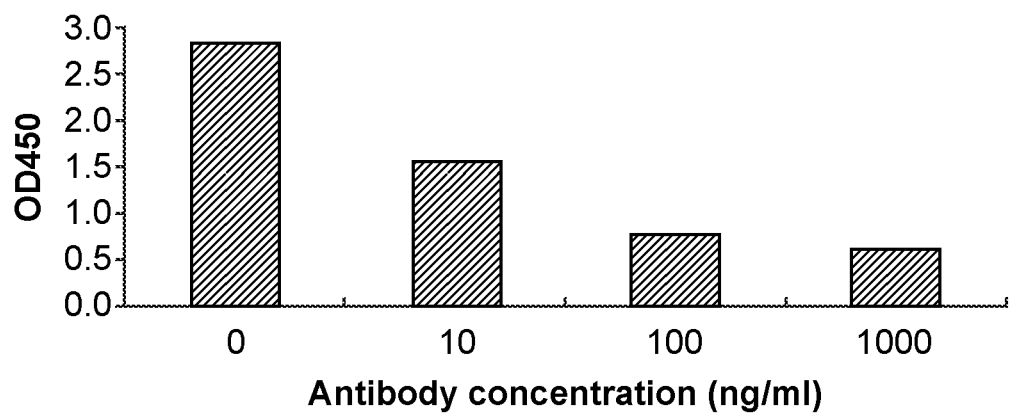

The results are shown in FIG. 5, panels 5A-5B, showing that the antibodies of the present invention can effectively inhibit TARC and MDC release, and the inhibitory effect on release increases with the increasing of antibody concentration.

Example 10: Effect of Specific Amino Acids on the Pharmacokinetics and Expression Levels of the Antibodies of the Invention In vivo pharmacokinetics of the antibodies of the invention are further detected and compared in this Example, in order to investigate the possible effects of specific amino acids at specific positions on the pharmacokinetics of the antibodies in animals. The specific experimental method was the same as that described in Example 4, and the results are shown in Table 9 below.

TABLE 9

Detection results of in vivo pharmacokinetics of the antibodies of the present invention

| | | Half life h | Time to peak h | Peak concentration ug/ml | Area Under the drug-time Curve h*ug/ml | Volume of distribution ml/kg | Clearance rate ml/h/kg |
|---|---|---|---|---|---|---|---|
| L1020H1031 | Mean value | 185.49 | 40 | 38.94 | 8188.8 | 114.28 | 0.43 |
| | Standard deviation | 18.52 | 13.86 | 2.33 | 510.47 | 6.5 | 0.05 |
| L1012H1001 | Mean value | 161.26 | 48.00 | 12.36 | 2491.19 | 332.79 | 1.47 |
| | Standard deviation | 54.30 | 0.00 | 2.26 | 165.16 | 76.91 | 0.20 |
| L1001H1031 | Mean value | 171.41 | 56.00 | 42.74 | 9273.73 | 99.17 | 0.40 |
| | Standard deviation | 6.12 | 13.86 | 7.38 | 1868.66 | 18.69 | 0.07 |
| L1020H1001 | Mean value | 89.00 | 64.00 | 20.11 | 3481.40 | 164.14 | 1.30 |
| | Standard deviation | 16.70 | 13.86 | 2.14 | 268.39 | 22.86 | 0.20 | investigate the possible effects of specific amino acids at specific positions on the expression of the antibodies. Culture and transfection of Expi293 cells were conducted according to Example 1, and the collected culture supernatant was then passed through a 0.22 μm filter and then purified by GE MabSelect Sure (Catalog Number: 11003494) Protein A affinity chromatography column in the purification system GE AKTA purifier 10. The purified antibody was collected and concentrated using Amicon ultrafiltration concentrating tube (Catalog Number: UFC903096) and then quantified. The quantitative results are shown in Table 10 below.

TABLE 10

Detection results of the expression levels of the antibodies of the present invention

| Antibody | Expression level ($\times 10^{-2}$ mg/ml culture medium) |
|---|---|
| L1020H1031 | 8.39 |
| L1001H1031 | 1.79 |
| L1020H1001 | 4.04 |
| L1012H1001 | 5.00 |
| L1023H1001 | 4.63 |
| L1001H1001 | 1.75 |

From the specific sequence, the amino acid at position 31 in the sequence of the light chain L1012 (SEQ ID NO. 44), From the specific sequence, the amino acid at position 103 in the sequence of the heavy chain H1031 (SEQ ID NO. 91) of the antibody (in CDR3) is Asp (103Asp), and the amino acid at position 104 is Tyr (104Tyr). Compared with antibodies that have no 103Asp and 104Tyr in heavy chain, the present antibodies which have 103Asp and 104Tyr have a 2- to 4-fold higher area under the drug-time curve and an about 70% reduced clearance rate.

The expression levels of the antibodies of the present invention are also detected and compared, in order to L1020 (SEQ ID NO. 55) or L1023 (SEQ ID NO. 51) of the antibody (in CDR1) is Ser (31Ser). Compared with antibodies that have no 31Ser in light chain, the present antibodies which have 31Ser have a 2- to 5-fold higher expression level.

The above description for the embodiments of the present invention is not intended to limit the present invention, and those skilled in the art can make various changes and variations according to the present invention, which are within the protection scope of the claims of the present invention without departing from the spirit of the same.

The invention claimed is:

1. A method of treating or ameliorating inflammation or allergic disease in a subject in need thereof, comprising administering to the subject an isolated anti-interleukin 4 receptor (IL-4R) antibody comprising a heavy chain variable domain (VH) comprising three heavy chain complementarity determining regions (CDRs) (CDR-H1, CDR-H2, and CDR-H3), and a light chain variable domain (VL) comprising three light chain CDRs (CDR-L1, CDR-L2, and CDR-L3) wherein:
   a. the CDR-L1 comprises the amino acid sequence set forth in SEQ ID NO: 2, the CDR-L2 comprises the amino acid sequence set forth in SEQ ID NO: 3, the CDR-L3 comprises the amino acid sequence set forth in SEQ ID NO: 8, the CDR-H1 comprises the amino acid sequence set forth in SEQ ID NO: 14, the CDR-H2 comprises the amino acid sequence set forth in SEQ ID NO: 18, and the CDR-H3 comprises the amino acid sequence set forth in SEQ ID NO: 19;
   b. the CDR-L1 comprises the amino acid sequence set forth in SEQ ID NO: 2, the CDR-L2 comprises the amino acid sequence set forth in SEQ ID NO: 4, the CDR-L3 comprises the amino acid sequence set forth in SEQ ID NO: 8, the CDR-H1 comprises the amino acid sequence set forth in SEQ ID NO: 14, the CDR-H2 comprises the amino acid sequence set forth in SEQ ID NO: 18, and the CDR-H3 comprises the amino acid sequence set forth in SEQ ID NO: 19; or
   c. the CDR-L1 comprises the amino acid sequence set forth in SEQ ID NO: 2, the CDR-L2 comprises the amino acid sequence set forth in SEQ ID NO: 4, the CDR-L3 comprises the amino acid sequence set forth in SEQ ID NO: 5, the CDR-H1 comprises the amino acid sequence set forth in SEQ ID NO: 14, the CDR-H2 comprises the amino acid sequence set forth in SEQ ID NO: 18, and the CDR-H3 comprises the amino acid sequence set forth in SEQ ID NO: 19.

2. The method of claim 1, wherein:
a. the VL comprises the amino acid sequence set forth in SEQ ID NO: 55 and the VH comprises the amino acid sequence set forth in SEQ ID NO: 91;
b. the VL comprises the amino acid sequence set forth in SEQ ID NO: 54 and the VH comprises the amino acid sequence set forth in SEQ ID NO: 91; or
c. the VL comprises the amino acid sequence set forth in SEQ ID NO: 44 and the VH chain sequence comprises the amino acid sequence set forth in SEQ ID NO: 91.

3. The method of claim 1, wherein the isolated antibody binds to human IL-4Rα.

4. The method of claim 1, wherein the isolated antibody binds to soluble human IL-4Rα.

5. The method of claim 1, wherein the isolated antibody is a monoclonal antibody.

6. The method of claim 1, wherein the isolated antibody is an immunoglobulin having a human isotype of IgA, IgD, IgE, IgG or IgM.

7. The method of claim 1, wherein the isolated antibody is a human IgG1, IgG2, IgG3, or IgG4 subtype.

8. The method of claim 1, wherein the isolated antibody is a human IgG4 subtype.

9. The method of claim 1, wherein the inflammation or allergic disease comprises atopic dermatitis.

10. The method of claim 1, wherein the inflammation or allergic disease comprises asthma.

11. The method of claim 1, wherein the CDR-L1 comprises the amino acid sequence set forth in SEQ ID NO: 2, the CDR-L2 comprises the amino acid sequence set forth in SEQ ID NO: 3, the CDR-L3 comprises the amino acid sequence set forth in SEQ ID NO: 8, the CDR-H1 comprises the amino acid sequence set forth in SEQ ID NO: 14, the CDR-H2 comprises the amino acid sequence set forth in SEQ ID NO: 18, and the CDR-H3 comprises the amino acid sequence set forth in SEQ ID NO: 19.

12. The method of claim 11, wherein the isolated antibody is a monoclonal antibody.

13. The method of claim 11, wherein the inflammation or allergic disease is selected from the group consisting of allergic dermatitis, asthma, eosinophilic esophagitis, eczema, allergic rhinitis, nasal polyp, and rheumatoid arthritis.

14. The method of claim 11, wherein the inflammation or allergic disease is an autoimmune disease.

15. The method of claim 11, wherein the inflammation or allergic disease is atopic dermatitis.

16. The method of claim 11, wherein the inflammation or allergic disease is asthma.

17. The method of claim 11, wherein the isolated antibody is a human IgG4 subtype.

18. The method of claim 1, wherein the CDR-L1 comprises the amino acid sequence set forth in SEQ ID NO: 2, the CDR-L2 comprises the amino acid sequence set forth in SEQ ID NO: 4, the CDR-L3 comprises the amino acid sequence set forth in SEQ ID NO: 8, the CDR-H1 comprises the amino acid sequence set forth in SEQ ID NO: 14, the CDR-H2 comprises the amino acid sequence set forth in SEQ ID NO: 18, and the CDR-H3 comprises the amino acid sequence set forth in SEQ ID NO: 19.

19. The method of claim 1, wherein the CDR-L1 comprises the amino acid sequence set forth in SEQ ID NO: 2, the CDR-L2 comprises the amino acid sequence set forth in SEQ ID NO: 4, the CDR-L3 comprises the amino acid sequence set forth in SEQ ID NO: 5, the CDR-H1 comprises the amino acid sequence set forth in SEQ ID NO: 14, the CDR-H2 comprises the amino acid sequence set forth in SEQ ID NO: 18, and the CDR-H3 comprises the amino acid sequence set forth in SEQ ID NO: 19.

20. The method of claim 1, wherein the VL comprises the amino acid sequence set forth in SEQ ID NO: 55 and the VH comprises the amino acid sequence set forth in SEQ ID NO: 91.

21. The method of claim 20, wherein the isolated antibody is a monoclonal antibody.

22. The method of claim 20, wherein the inflammation or allergic disease is an autoimmune disease.

23. The method of claim 20, wherein the inflammation or allergic disease is selected from the group consisting of allergic dermatitis, asthma, eosinophilic esophagitis, eczema, allergic rhinitis, nasal polyp, and rheumatoid arthritis.

24. The method of claim 20, wherein the inflammation or allergic disease is atopic dermatitis.

25. The method of claim 20, wherein the inflammation or allergic disease is asthma.

26. The method of claim 20, wherein the isolated antibody is a human IgG4 subtype.

27. The method of claim 1, wherein the VL comprises the amino acid sequence set forth in SEQ ID NO: 54 and the VH comprises the amino acid sequence set forth in SEQ ID NO: 91.

28. The method of claim 1, wherein the VL comprises the amino acid sequence set forth in SEQ ID NO: 44 and the VH comprises the amino acid sequence set forth in SEQ ID NO: 91.

29. The method of claim 1, wherein the inflammation or allergic disease is an autoimmune disease.

30. The method of claim 1, wherein the inflammation or allergic disease is selected from the group consisting of allergic dermatitis, asthma, eosinophilic esophagitis, eczema, allergic rhinitis, nasal polyp, and rheumatoid arthritis.

31. The method of claim 1, wherein the inflammation or allergic disease is atopic dermatitis.

32. The method of claim 1, wherein the inflammation or allergic disease is asthma.

* * * * *

UNITED STATES PATENT AND TRADEMARK OFFICE
CERTIFICATE OF CORRECTION

| | |
|---|---|
| PATENT NO. | : 11,866,491 B2 |
| APPLICATION NO. | : 16/994464 |
| DATED | : January 9, 2024 |
| INVENTOR(S) | : Wei Zheng et al. |

It is certified that error appears in the above-identified patent and that said Letters Patent is hereby corrected as shown below:

On the Title Page

In Column 1, at Item (73) Assignee, delete "SuZhou Connect Biopharmaceuticals, Inc." and insert -- SuZhou Connect Biopharmaceuticals, Ltd. --.

In Column 1, at Item (60) under Related U.S. Application Data, Line 3, delete "continuation-in-part" and insert -- continuation --.

In the Claims

In Column 92, Line 53, delete ""scquence" and insert -- sequence --.

Signed and Sealed this
Tenth Day of September, 2024

Katherine Kelly Vidal
*Director of the United States Patent and Trademark Office*

SEQUENCE LISTING

<160> NUMBER OF SEQ ID NOS: 94

<210> SEQ ID NO 1
<211> LENGTH: 12
<212> TYPE: PRT
<213> ORGANISM: Artificial sequence
<220> FEATURE:
<223> OTHER INFORMATION: LCDR1-1

<400> SEQUENCE: 1

Arg Ala Ser Gln Ser Val Ser Asn Ser Tyr Leu Ala
1               5                   10

<210> SEQ ID NO 2
<211> LENGTH: 12
<212> TYPE: PRT
<213> ORGANISM: Artificial sequence
<220> FEATURE:
<223> OTHER INFORMATION: LCDR1-2

<400> SEQUENCE: 2

Arg Ala Ser Gln Ser Val Ser Ser Ser Tyr Leu Ala
1               5                   10

<210> SEQ ID NO 3
<211> LENGTH: 7
<212> TYPE: PRT
<213> ORGANISM: Artificial sequence
<220> FEATURE:
<223> OTHER INFORMATION: LCDR2-1

<400> SEQUENCE: 3

Gly Ala Ser Ser Arg Ala Thr
1               5

<210> SEQ ID NO 4
<211> LENGTH: 7
<212> TYPE: PRT
<213> ORGANISM: Artificial sequence
<220> FEATURE:
<223> OTHER INFORMATION: LCDR2-2

<400> SEQUENCE: 4

Gly Ala Ser Ser Arg Ala Pro
1               5

<210> SEQ ID NO 5
<211> LENGTH: 10
<212> TYPE: PRT
<213> ORGANISM: Artificial sequence
<220> FEATURE:
<223> OTHER INFORMATION: LCDR3-1

<400> SEQUENCE: 5

Gln Gln Tyr Gly Ser Ser Pro Pro Trp Thr
1               5                   10

<210> SEQ ID NO 6
<211> LENGTH: 10
<212> TYPE: PRT
<213> ORGANISM: Artificial sequence
<220> FEATURE:
<223> OTHER INFORMATION: LCDR3-2

<400> SEQUENCE: 6

Gln Gln Tyr Asp His Ser Pro Pro Trp Thr
1               5                   10

<210> SEQ ID NO 7
<211> LENGTH: 10
<212> TYPE: PRT
<213> ORGANISM: Artificial sequence
<220> FEATURE:
<223> OTHER INFORMATION: LCDR3-3

<400> SEQUENCE: 7

Gln Gln Tyr Gly Ser Ser Ala Gly Trp Thr
1               5                   10

<210> SEQ ID NO 8
<211> LENGTH: 10
<212> TYPE: PRT
<213> ORGANISM: Artificial sequence
<220> FEATURE:
<223> OTHER INFORMATION: LCDR3-4

<400> SEQUENCE: 8

Gln Gln Tyr Asp His Ser Ala Gly Trp Thr
1               5                   10

<210> SEQ ID NO 9
<211> LENGTH: 23
<212> TYPE: PRT
<213> ORGANISM: Artificial sequence
<220> FEATURE:
<223> OTHER INFORMATION: LFR1-1

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 10
<211> LENGTH: 15
<212> TYPE: PRT
<213> ORGANISM: Artificial sequence
<220> FEATURE:
<223> OTHER INFORMATION: LFR2-1

<400> SEQUENCE: 10

Trp Tyr Gln Gln Lys Pro Gly Gln Ala Pro Arg Leu Leu Ile Phe
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: LFR2-2

<400> SEQUENCE: 11

Trp Tyr Gln Gln Lys Pro Gly Gln Ala Pro Arg Leu Leu Ile Tyr
1               5                   10                  15

<210> SEQ ID NO 12
<211> LENGTH: 32
<212> TYPE: PRT
<213> ORGANISM: Artificial sequence
<220> FEATURE:
<223> OTHER INFORMATION: LFR3-1

<400> SEQUENCE: 12

```
Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 13
<211> LENGTH: 10
<212> TYPE: PRT
<213> ORGANISM: Artificial sequence
<220> FEATURE:
<223> OTHER INFORMATION: LFR4-1

<400> SEQUENCE: 13

Phe Gly Gln Gly Thr Lys Val Glu Ile Lys
1               5                   10

<210> SEQ ID NO 14
<211> LENGTH: 5
<212> TYPE: PRT
<213> ORGANISM: Artificial sequence
<220> FEATURE:
<223> OTHER INFORMATION: HCDR1-1

<400> SEQUENCE: 14

Arg Asn Ala Met Phe
1               5

<210> SEQ ID NO 15
<211> LENGTH: 5
<212> TYPE: PRT
<213> ORGANISM: Artificial sequence
<220> FEATURE:
<223> OTHER INFORMATION: HCDR1-2

<400> SEQUENCE: 15

Arg Asn Ala Met His
1               5

<210> SEQ ID NO 16
<211> LENGTH: 5
<212> TYPE: PRT
<213> ORGANISM: Artificial sequence
<220> FEATURE:
<223> OTHER INFORMATION: HCDR1-3

<400> SEQUENCE: 16

Asp Tyr Ala Met Phe
1               5

<210> SEQ ID NO 17
<211> LENGTH: 17
<212> TYPE: PRT
<213> ORGANISM: Artificial sequence
<220> FEATURE:
<223> OTHER INFORMATION: HCDR2-1

<400> SEQUENCE: 17

Gly Ile Gly Thr Gly Gly Ala Thr Asn Tyr Ala Asp Ser Val Lys Gly
1               5                   10                  15

Arg

<210> SEQ ID NO 18
<211> LENGTH: 17
<212> TYPE: PRT
<213> ORGANISM: Artificial sequence
<220> FEATURE:
```

<223> OTHER INFORMATION: HCDR2-2

<400> SEQUENCE: 18

Gly Ile Gly Thr Gly Gly Ala Thr Ser Tyr Ala Asp Ser Val Lys Gly
1               5                   10                  15

Arg

<210> SEQ ID NO 19
<211> LENGTH: 7
<212> TYPE: PRT
<213> ORGANISM: Artificial sequence
<220> FEATURE:
<223> OTHER INFORMATION: HCDR3-1

<400> SEQUENCE: 19

Gly Arg Tyr Tyr Phe Asp Tyr
1               5

<210> SEQ ID NO 20
<211> LENGTH: 7
<212> TYPE: PRT
<213> ORGANISM: Artificial sequence
<220> FEATURE:
<223> OTHER INFORMATION: HCDR3-2

<400> SEQUENCE: 20

Gly Arg Tyr Tyr Phe Pro Trp
1               5

<210> SEQ ID NO 21
<211> LENGTH: 30
<212> TYPE: PRT
<213> ORGANISM: Artificial sequence
<220> FEATURE:
<223> OTHER INFORMATION: HFR1-1

<400> SEQUENCE: 21

Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser
            20                  25                  30

<210> SEQ ID NO 22
<211> LENGTH: 30
<212> TYPE: PRT
<213> ORGANISM: Artificial sequence
<220> FEATURE:
<223> OTHER INFORMATION: HFR1-2

<400> SEQUENCE: 22

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser
            20                  25                  30

<210> SEQ ID NO 23
<211> LENGTH: 30
<212> TYPE: PRT
<213> ORGANISM: Artificial sequence
<220> FEATURE:
<223> OTHER INFORMATION: HFR1-3

<400> SEQUENCE: 23

Glu Val Gln Leu Val Gln Ser Gly Gly Gly Leu Val His Pro Gly Gly
1               5                   10                  15

Ser Leu Arg Leu Ser Cys Ala Ala Ser Gly Phe Thr Phe Ser
            20                  25                  30

<210> SEQ ID NO 24
<211> LENGTH: 30
<212> TYPE: PRT
<213> ORGANISM: Artificial sequence
<220> FEATURE:
<223> OTHER INFORMATION: HFR1-4

<400> SEQUENCE: 24

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser
            20                  25                  30

<210> SEQ ID NO 25
<211> LENGTH: 30
<212> TYPE: PRT
<213> ORGANISM: Artificial sequence
<220> FEATURE:
<223> OTHER INFORMATION: HFR1-5

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser
            20                  25                  30

<210> SEQ ID NO 26
<211> LENGTH: 30
<212> TYPE: PRT
<213> ORGANISM: Artificial sequence
<220> FEATURE:
<223> OTHER INFORMATION: HFR1-6

<400> SEQUENCE: 26

Glu Val Gln Leu Val Glu Ser Gly Gly Gly Leu Val His Pro Gly Gly
1               5                   10                  15

Ser Leu Arg Leu Ser Cys Ala Ala Ser Gly Phe Thr Phe Ser
            20                  25                  30

<210> SEQ ID NO 27
<211> LENGTH: 30
<212> TYPE: PRT
<213> ORGANISM: Artificial sequence
<220> FEATURE:
<223> OTHER INFORMATION: HFR1-7

<400> SEQUENCE: 27

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 28
<211> LENGTH: 30
<212> TYPE: PRT
<213> ORGANISM: Artificial sequence
<220> FEATURE:
<223> OTHER INFORMATION: HFR1-8

<400> SEQUENCE: 28

Glu Val Gln Leu Val Glu Ser Gly Gly Gly Leu Val Gln Pro Gly Gly

```
                1               5                  10                  15
Ser Leu Arg Leu Ser Cys Ala Ala Ser Gly Phe Thr Phe Ser
            20                  25                  30

<210> SEQ ID NO 29
<211> LENGTH: 30
<212> TYPE: PRT
<213> ORGANISM: Artificial sequence
<220> FEATURE:
<223> OTHER INFORMATION: HFR1-9

<400> SEQUENCE: 29

Glu Val Gln Leu Val Gln Ser Gly Gly Gly Leu Val His Pro Gly Arg
1               5                  10                  15
Ser Leu Arg Leu Ser Cys Ala Gly Ser Gly Phe Thr Phe Ser
            20                  25                  30

<210> SEQ ID NO 30
<211> LENGTH: 30
<212> TYPE: PRT
<213> ORGANISM: Artificial sequence
<220> FEATURE:
<223> OTHER INFORMATION: HFR1-10

<400> SEQUENCE: 30

Glu Val Gln Leu Val Gln Ser Gly Gly Gly Leu Val His Pro Gly Gly
1               5                  10                  15
Ser Leu Arg Leu Thr Cys Ala Gly Ser Gly Phe Thr Phe Ser
            20                  25                  30

<210> SEQ ID NO 31
<211> LENGTH: 30
<212> TYPE: PRT
<213> ORGANISM: Artificial sequence
<220> FEATURE:
<223> OTHER INFORMATION: HFR1-11

<400> SEQUENCE: 31

Glu Val Gln Leu Val Gln Ser Gly Gly Gly Leu Val His Pro Gly Gly
1               5                  10                  15
Ser Leu Arg Leu Ser Cys Ala Gly Ser Gly Phe Thr Phe Asp
            20                  25                  30

<210> SEQ ID NO 32
<211> LENGTH: 14
<212> TYPE: PRT
<213> ORGANISM: Artificial sequence
<220> FEATURE:
<223> OTHER INFORMATION: HFR2-1

<400> SEQUENCE: 32

Trp Val Arg Gln Ala Pro Gly Lys Gly Leu Glu Trp Val Ser
1               5                  10

<210> SEQ ID NO 33
<211> LENGTH: 14
<212> TYPE: PRT
<213> ORGANISM: Artificial sequence
<220> FEATURE:
<223> OTHER INFORMATION: HFR2-2

<400> SEQUENCE: 33

Trp Val Arg Gln Ala Pro Gly Glu Gly Leu Glu Trp Val Ser
1               5                  10
```

<210> SEQ ID NO 34
<211> LENGTH: 31
<212> TYPE: PRT
<213> ORGANISM: Artificial sequence
<220> FEATURE:
<223> OTHER INFORMATION: HFR3-1

<400> SEQUENCE: 34

Phe Thr Ile Ser Arg Asp Asn Ala Lys Asn Ser Leu Tyr Leu Gln Met
1               5                   10                  15

Asn Ser Leu Arg Ala Glu Asp Met Ala Val Tyr Tyr Cys Ala Arg
            20                  25                  30

<210> SEQ ID NO 35
<211> LENGTH: 31
<212> TYPE: PRT
<213> ORGANISM: Artificial sequence
<220> FEATURE:
<223> OTHER INFORMATION: HFR3-2

<400> SEQUENCE: 35

Phe Thr Ile Ser Arg Asp Asn Ala Lys Asn Ser Leu Tyr Leu Gln Met
1               5                   10                  15

Asn Ser Leu Arg Ala Glu Asp Thr Ala Val Tyr Tyr Cys Ala Arg
            20                  25                  30

<210> SEQ ID NO 36
<211> LENGTH: 31
<212> TYPE: PRT
<213> ORGANISM: Artificial sequence
<220> FEATURE:
<223> OTHER INFORMATION: HFR3-3

<400> SEQUENCE: 36

Phe Thr Ile Ser Arg Asp Glu Ala Lys Asn Ser Leu Tyr Leu Gln Met
1               5                   10                  15

Asn Ser Leu Arg Ala Glu Asp Met Ala Val Tyr Tyr Cys Ala Arg
            20                  25                  30

<210> SEQ ID NO 37
<211> LENGTH: 31
<212> TYPE: PRT
<213> ORGANISM: Artificial sequence
<220> FEATURE:
<223> OTHER INFORMATION: HFR3-4

<400> SEQUENCE: 37

Phe Thr Ile Ser Arg Asp Asn Ala Lys Asn Ser Leu Tyr Leu Gln Met
1               5                   10                  15

Asn Ser Leu Arg Ala Gly Asp Met Ala Val Tyr Tyr Cys Ala Arg
            20                  25                  30

<210> SEQ ID NO 38
<211> LENGTH: 11
<212> TYPE: PRT
<213> ORGANISM: Artificial sequence
<220> FEATURE:
<223> OTHER INFORMATION: HFR4-1

<400> SEQUENCE: 38

Trp Gly Gln Gly Thr Leu Val Thr Val Ser Ser
1               5                   10

<210> SEQ ID NO 39

```
<211> LENGTH: 109
<212> TYPE: PRT
<213> ORGANISM: Artificial sequence
<220> FEATURE:
<223> OTHER INFORMATION: VL L1007

<400> SEQUENCE: 39

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ser
            20                  25                  30

Tyr Leu Ala Trp Tyr Gln Gln Lys Pro Gly Gln Ala Pro Arg Leu Leu
        35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys
            100                 105

<210> SEQ ID NO 40
<211> LENGTH: 109
<212> TYPE: PRT
<213> ORGANISM: Artificial sequence
<220> FEATURE:
<223> OTHER INFORMATION: VL L1008

<400> SEQUENCE: 40

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys
            100                 105

<210> SEQ ID NO 41
<211> LENGTH: 109
<212> TYPE: PRT
<213> ORGANISM: Artificial sequence
<220> FEATURE:
<223> OTHER INFORMATION: VL L1009

<400> SEQUENCE: 41

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

```
Ile Phe Gly Ala Ser Ser Arg Ala Pro Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Trp Thr Phe Gly Gln Gly Thr Lys Val Glu Ile Lys
            100                 105
```

```
<210> SEQ ID NO 42
<211> LENGTH: 109
<212> TYPE: PRT
<213> ORGANISM: Artificial sequence
<220> FEATURE:
<223> OTHER INFORMATION: VL L1010

<400> SEQUENCE: 42

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Asn Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Trp Thr Phe Gly Gln Gly Thr Lys Val Glu Ile Lys
            100                 105
```

```
<210> SEQ ID NO 43
<211> LENGTH: 109
<212> TYPE: PRT
<213> ORGANISM: Artificial sequence
<220> FEATURE:
<223> OTHER INFORMATION: VL L1011

<400> SEQUENCE: 43

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Asn Ser
                20                  25                  30

Tyr Leu Ala Trp Tyr Gln Gln Lys Pro Gly Gln Ala Pro Arg Leu Leu
            35                  40                  45

Ile Phe Gly Ala Ser Ser Arg Ala Pro Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Trp Thr Phe Gly Gln Gly Thr Lys Val Glu Ile Lys
            100                 105
```

```
<210> SEQ ID NO 44
<211> LENGTH: 109
<212> TYPE: PRT
<213> ORGANISM: Artificial sequence
```

```
<220> FEATURE:
<223> OTHER INFORMATION: VL L1012

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys
            100                 105

<210> SEQ ID NO 45
<211> LENGTH: 109
<212> TYPE: PRT
<213> ORGANISM: Artificial sequence
<220> FEATURE:
<223> OTHER INFORMATION: VL L1016

<400> SEQUENCE: 45

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp His Ser Pro
                85                  90                  95

Pro Trp Thr Phe Gly Gln Gly Thr Lys Val Glu Ile Lys
            100                 105

<210> SEQ ID NO 46
<211> LENGTH: 109
<212> TYPE: PRT
<213> ORGANISM: Artificial sequence
<220> FEATURE:
<223> OTHER INFORMATION: VL L1017

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Phe Gly Ala Ser Ser Arg Ala Thr Gly Ile Pro Asp Arg Phe Ser
    50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ala
                85                  90                  95

Gly Trp Thr Phe Gly Gln Gly Thr Lys Val Glu Ile Lys
            100                 105

<210> SEQ ID NO 47
<211> LENGTH: 109
<212> TYPE: PRT
<213> ORGANISM: Artificial sequence
<220> FEATURE:
<223> OTHER INFORMATION: VL L1018

<400> SEQUENCE: 47

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp His Ser Ala
                85                  90                  95

Gly Trp Thr Phe Gly Gln Gly Thr Lys Val Glu Ile Lys
            100                 105

<210> SEQ ID NO 48
<211> LENGTH: 109
<212> TYPE: PRT
<213> ORGANISM: Artificial sequence
<220> FEATURE:
<223> OTHER INFORMATION: VL L1013

<400> SEQUENCE: 48

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ser
                20                  25                  30

Tyr Leu Ala Trp Tyr Gln Gln Lys Pro Gly Gln Ala Pro Arg Leu Leu
            35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp His Ser Pro
                85                  90                  95

Pro Trp Thr Phe Gly Gln Gly Thr Lys Val Glu Ile Lys
            100                 105

<210> SEQ ID NO 49
<211> LENGTH: 109
<212> TYPE: PRT
<213> ORGANISM: Artificial sequence
<220> FEATURE:
<223> OTHER INFORMATION: VL L1014

```
<400> SEQUENCE: 49

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp His Ser Pro
                85                  90                  95

Pro Trp Thr Phe Gly Gln Gly Thr Lys Val Glu Ile Lys
            100                 105

<210> SEQ ID NO 50
<211> LENGTH: 109
<212> TYPE: PRT
<213> ORGANISM: Artificial sequence
<220> FEATURE:
<223> OTHER INFORMATION: VL L1015

<400> SEQUENCE: 50

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Phe Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp His Ser Pro
                85                  90                  95

Pro Trp Thr Phe Gly Gln Gly Thr Lys Val Glu Ile Lys
            100                 105

<210> SEQ ID NO 51
<211> LENGTH: 109
<212> TYPE: PRT
<213> ORGANISM: Artificial sequence
<220> FEATURE:
<223> OTHER INFORMATION: VL L1023

<400> SEQUENCE: 51

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Asp His Ser Ala
                85                  90                  95

Gly Trp Thr Phe Gly Gln Gly Thr Lys Val Glu Ile Lys
            100                 105

<210> SEQ ID NO 52
<211> LENGTH: 109
<212> TYPE: PRT
<213> ORGANISM: Artificial sequence
<220> FEATURE:
<223> OTHER INFORMATION: VL L1024

<400> SEQUENCE: 52

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ser
                20                  25                  30

Tyr Leu Ala Trp Tyr Gln Gln Lys Pro Gly Gln Ala Pro Arg Leu Leu
            35                  40                  45

Ile Phe Gly Ala Ser Ser Arg Ala Pro Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp His Ser Ala
                85                  90                  95

Gly Trp Thr Phe Gly Gln Gly Thr Lys Val Glu Ile Lys
            100                 105

<210> SEQ ID NO 53
<211> LENGTH: 109
<212> TYPE: PRT
<213> ORGANISM: Artificial sequence
<220> FEATURE:
<223> OTHER INFORMATION: VL L1022

<400> SEQUENCE: 53

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp His Ser Ala
                85                  90                  95

Gly Trp Thr Phe Gly Gln Gly Thr Lys Val Glu Ile Lys
            100                 105

<210> SEQ ID NO 54
<211> LENGTH: 109
<212> TYPE: PRT
<213> ORGANISM: Artificial sequence
<220> FEATURE:
<223> OTHER INFORMATION: VL L1021

<400> SEQUENCE: 54

Glu Ile Val Leu Thr Gln Ser Pro Gly Thr Leu Ser Leu Ser Pro Gly
```

```
1               5                  10                 15
Glu Arg Ala Thr Leu Ser Cys Arg Ala Ser Gln Ser Val Ser Ser Ser
                20                 25                 30

Tyr Leu Ala Trp Tyr Gln Gln Lys Pro Gly Gln Ala Pro Arg Leu Leu
            35                 40                 45

Ile Phe Gly Ala Ser Ser Arg Ala Pro Gly Ile Pro Asp Arg Phe Ser
        50                 55                 60

Gly Ser Gly Ser Gly Thr Asp Phe Thr Leu Thr Ile Ser Arg Leu Glu
65                  70                 75                  80

Pro Glu Asp Phe Ala Val Tyr Tyr Cys Gln Gln Tyr Asp His Ser Ala
                85                 90                 95

Gly Trp Thr Phe Gly Gln Gly Thr Lys Val Glu Ile Lys
                100                105
```

<210> SEQ ID NO 55
<211> LENGTH: 109
<212> TYPE: PRT
<213> ORGANISM: Artificial sequence
<220> FEATURE:
<223> OTHER INFORMATION: VL L1020

<400> SEQUENCE: 55

```
Glu Ile Val Leu Thr Gln Ser Pro Gly Thr Leu Ser Leu Ser Pro Gly
1               5                  10                 15

Glu Arg Ala Thr Leu Ser Cys Arg Ala Ser Gln Ser Val Ser Ser Ser
                20                 25                 30

Tyr Leu Ala Trp Tyr Gln Gln Lys Pro Gly Gln Ala Pro Arg Leu Leu
            35                 40                 45

Ile Tyr Gly Ala Ser Ser Arg Ala Thr Gly Ile Pro Asp Arg Phe Ser
        50                 55                 60

Gly Ser Gly Ser Gly Thr Asp Phe Thr Leu Thr Ile Ser Arg Leu Glu
65                  70                 75                  80

Pro Glu Asp Phe Ala Val Tyr Tyr Cys Gln Gln Tyr Asp His Ser Ala
                85                 90                 95

Gly Trp Thr Phe Gly Gln Gly Thr Lys Val Glu Ile Lys
                100                105
```

<210> SEQ ID NO 56
<211> LENGTH: 109
<212> TYPE: PRT
<213> ORGANISM: Artificial sequence
<220> FEATURE:
<223> OTHER INFORMATION: VL L1019

<400> SEQUENCE: 56

```
Glu Ile Val Leu Thr Gln Ser Pro Gly Thr Leu Ser Leu Ser Pro Gly
1               5                  10                 15

Glu Arg Ala Thr Leu Ser Cys Arg Ala Ser Gln Ser Val Ser Asn Ser
                20                 25                 30

Tyr Leu Ala Trp Tyr Gln Gln Lys Pro Gly Gln Ala Pro Arg Leu Leu
            35                 40                 45

Ile Phe Gly Ala Ser Ser Arg Ala Thr Gly Ile Pro Asp Arg Phe Ser
        50                 55                 60

Gly Ser Gly Ser Gly Thr Asp Phe Thr Leu Thr Ile Ser Arg Leu Glu
65                  70                 75                  80

Pro Glu Asp Phe Ala Val Tyr Tyr Cys Gln Gln Tyr Asp His Ser Ala
                85                 90                 95
```

Gly Trp Thr Phe Gly Gln Gly Thr Lys Val Glu Ile Lys
            100                 105

<210> SEQ ID NO 57
<211> LENGTH: 109
<212> TYPE: PRT
<213> ORGANISM: Artificial sequence
<220> FEATURE:
<223> OTHER INFORMATION: VL L1000

<400> SEQUENCE: 57

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys
            100                 105

<210> SEQ ID NO 58
<211> LENGTH: 109
<212> TYPE: PRT
<213> ORGANISM: Artificial sequence
<220> FEATURE:
<223> OTHER INFORMATION: VL L1001

<400> SEQUENCE: 58

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp His Ser Ala
                85                  90                  95

Gly Trp Thr Phe Gly Gln Gly Thr Lys Val Glu Ile Lys
            100                 105

<210> SEQ ID NO 59
<211> LENGTH: 115
<212> TYPE: PRT
<213> ORGANISM: Artificial sequence
<220> FEATURE:
<223> OTHER INFORMATION: VH H1009

<400> SEQUENCE: 59

Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Arg Asn

```
                    20                  25                  30
Ala Met Phe Trp Val Arg Gln Ala Pro Gly Lys Gly Leu Glu Trp Val
            35                  40                  45

Ser Gly Ile Gly Thr Gly Gly Ala Thr Asn Tyr Ala Asp Ser Val Lys
        50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115

<210> SEQ ID NO 60
<211> LENGTH: 115
<212> TYPE: PRT
<213> ORGANISM: Artificial sequence
<220> FEATURE:
<223> OTHER INFORMATION: VH H1010

<400> SEQUENCE: 60

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
            35                  40                  45

Ser Gly Ile Gly Thr Gly Gly Ala Thr Asn Tyr Ala Asp Ser Val Lys
        50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115

<210> SEQ ID NO 61
<211> LENGTH: 115
<212> TYPE: PRT
<213> ORGANISM: Artificial sequence
<220> FEATURE:
<223> OTHER INFORMATION: VH H1011

<400> SEQUENCE: 61

Glu Val Gln Leu Val Gln Ser Gly Gly Gly Leu Val His Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
            35                  40                  45

Ser Gly Ile Gly Thr Gly Gly Ala Thr Asn Tyr Ala Asp Ser Val Lys
        50                  55                  60

Gly Arg Phe Thr Ile Ser Arg Asp Asn Ala Lys Asn Ser Leu Tyr Leu
65                  70                  75                  80
```

-continued

```
Gln Met Asn Ser Leu Arg Ala Glu Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115

<210> SEQ ID NO 62
<211> LENGTH: 115
<212> TYPE: PRT
<213> ORGANISM: Artificial sequence
<220> FEATURE:
<223> OTHER INFORMATION: VH H1007

<400> SEQUENCE: 62

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115

<210> SEQ ID NO 63
<211> LENGTH: 115
<212> TYPE: PRT
<213> ORGANISM: Artificial sequence
<220> FEATURE:
<223> OTHER INFORMATION: VH H1008

<400> SEQUENCE: 63

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115

<210> SEQ ID NO 64
```

```
<211> LENGTH: 115
<212> TYPE: PRT
<213> ORGANISM: Artificial sequence
<220> FEATURE:
<223> OTHER INFORMATION: VH H1015

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115

<210> SEQ ID NO 65
<211> LENGTH: 115
<212> TYPE: PRT
<213> ORGANISM: Artificial sequence
<220> FEATURE:
<223> OTHER INFORMATION: VH H1013

<400> SEQUENCE: 65

Glu Val Gln Leu Val Glu Ser Gly Gly Gly Leu Val His Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115

<210> SEQ ID NO 66
<211> LENGTH: 115
<212> TYPE: PRT
<213> ORGANISM: Artificial sequence
<220> FEATURE:
<223> OTHER INFORMATION: VH H1014

<400> SEQUENCE: 66

Glu Val Gln Leu Val Gln Ser Gly Gly Gly Leu Val Gln Pro Gly Gly
1               5                   10                  15
```

```
Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115

<210> SEQ ID NO 67
<211> LENGTH: 115
<212> TYPE: PRT
<213> ORGANISM: Artificial sequence
<220> FEATURE:
<223> OTHER INFORMATION: VH H1012

<400> SEQUENCE: 67

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115

<210> SEQ ID NO 68
<211> LENGTH: 115
<212> TYPE: PRT
<213> ORGANISM: Artificial sequence
<220> FEATURE:
<223> OTHER INFORMATION: VH H1016

<400> SEQUENCE: 68

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80
```

Gln Met Asn Ser Leu Arg Ala Glu Asp Met Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115

<210> SEQ ID NO 69
<211> LENGTH: 115
<212> TYPE: PRT
<213> ORGANISM: Artificial sequence
<220> FEATURE:
<223> OTHER INFORMATION: VH H1017

<400> SEQUENCE: 69

Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115

<210> SEQ ID NO 70
<211> LENGTH: 115
<212> TYPE: PRT
<213> ORGANISM: Artificial sequence
<220> FEATURE:
<223> OTHER INFORMATION: VH H1018

<400> SEQUENCE: 70

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115

```
<210> SEQ ID NO 71
<211> LENGTH: 115
<212> TYPE: PRT
<213> ORGANISM: Artificial sequence
<220> FEATURE:
<223> OTHER INFORMATION: VH H1019

<400> SEQUENCE: 71

Glu Val Gln Leu Val Gln Ser Gly Gly Gly Leu Val His Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115

<210> SEQ ID NO 72
<211> LENGTH: 115
<212> TYPE: PRT
<213> ORGANISM: Artificial sequence
<220> FEATURE:
<223> OTHER INFORMATION: VH H1020

<400> SEQUENCE: 72

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115

<210> SEQ ID NO 73
<211> LENGTH: 115
<212> TYPE: PRT
<213> ORGANISM: Artificial sequence
<220> FEATURE:
<223> OTHER INFORMATION: VH H1021

<400> SEQUENCE: 73

Glu Val Gln Leu Val Gln Ser Gly Gly Gly Leu Val His Pro Gly Gly
1               5                   10                  15
```

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115

<210> SEQ ID NO 74
<211> LENGTH: 115
<212> TYPE: PRT
<213> ORGANISM: Artificial sequence
<220> FEATURE:
<223> OTHER INFORMATION: VH H1033

<400> SEQUENCE: 74

Glu Val Gln Leu Val Gln Ser Gly Gly Gly Leu Val His Pro Gly Arg
 1               5                  10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
 50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115

<210> SEQ ID NO 75
<211> LENGTH: 115
<212> TYPE: PRT
<213> ORGANISM: Artificial sequence
<220> FEATURE:
<223> OTHER INFORMATION: VH H1034

<400> SEQUENCE: 75

Glu Val Gln Leu Val Gln Ser Gly Gly Gly Leu Val His Pro Gly Gly
 1               5                  10                  15

Ser Leu Arg Leu Thr Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
 50                  55                  60

Gly Arg Phe Thr Ile Ser Arg Asp Asn Ala Lys Asn Ser Leu Tyr Leu

```
                65                  70                  75                  80
Gln Met Asn Ser Leu Arg Ala Glu Asp Met Ala Val Tyr Tyr Cys Ala
                    85                  90                  95

Arg Gly Arg Tyr Tyr Phe Asp Tyr Trp Gly Gln Gly Thr Leu Val Thr
                100                 105                 110

Val Ser Ser
        115

<210> SEQ ID NO 76
<211> LENGTH: 115
<212> TYPE: PRT
<213> ORGANISM: Artificial sequence
<220> FEATURE:
<223> OTHER INFORMATION: VH H1035

<400> SEQUENCE: 76

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
                20                  25                  30

Ala Met His Trp Val Arg Gln Ala Pro Gly Lys Gly Leu Glu Trp Val
                35                  40                  45

Ser Gly Ile Gly Thr Gly Gly Ala Thr Asn Tyr Ala Asp Ser Val Lys
        50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                    85                  90                  95

Arg Gly Arg Tyr Tyr Phe Asp Tyr Trp Gly Gln Gly Thr Leu Val Thr
                100                 105                 110

Val Ser Ser
        115

<210> SEQ ID NO 77
<211> LENGTH: 115
<212> TYPE: PRT
<213> ORGANISM: Artificial sequence
<220> FEATURE:
<223> OTHER INFORMATION: VH H1036

<400> SEQUENCE: 77

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
                20                  25                  30

Ala Met Phe Trp Val Arg Gln Ala Pro Gly Glu Gly Leu Glu Trp Val
                35                  40                  45

Ser Gly Ile Gly Thr Gly Gly Ala Thr Asn Tyr Ala Asp Ser Val Lys
        50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                    85                  90                  95

Arg Gly Arg Tyr Tyr Phe Asp Tyr Trp Gly Gln Gly Thr Leu Val Thr
                100                 105                 110

Val Ser Ser
        115
```

<210> SEQ ID NO 78
<211> LENGTH: 115
<212> TYPE: PRT
<213> ORGANISM: Artificial sequence
<220> FEATURE:
<223> OTHER INFORMATION: VH H1037

<400> SEQUENCE: 78

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Glu Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115
```

<210> SEQ ID NO 79
<211> LENGTH: 115
<212> TYPE: PRT
<213> ORGANISM: Artificial sequence
<220> FEATURE:
<223> OTHER INFORMATION: VH H1039

<400> SEQUENCE: 79

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Gly Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115
```

<210> SEQ ID NO 80
<211> LENGTH: 115
<212> TYPE: PRT
<213> ORGANISM: Artificial sequence
<220> FEATURE:
<223> OTHER INFORMATION: VH H1038

<400> SEQUENCE: 80

```
Glu Val Gln Leu Val Gln Ser Gly Gly Gly Leu Val His Pro Gly Gly
```

```
              1               5                  10                 15
Ser Leu Arg Leu Ser Cys Ala Gly Ser Gly Phe Thr Phe Asp Asp Tyr
              20                 25                 30

Ala Met Phe Trp Val Arg Gln Ala Pro Gly Lys Gly Leu Glu Trp Val
              35                 40                 45

Ser Gly Ile Gly Thr Gly Gly Ala Thr Asn Tyr Ala Asp Ser Val Lys
              50                 55                 60

Gly Arg Phe Thr Ile Ser Arg Asp Asn Ala Lys Asn Ser Leu Tyr Leu
 65               70                 75                 80

Gln Met Asn Ser Leu Arg Ala Glu Asp Met Ala Val Tyr Tyr Cys Ala
              85                 90                 95

Arg Gly Arg Tyr Tyr Phe Asp Tyr Trp Gly Gln Gly Thr Leu Val Thr
              100                105                110

Val Ser Ser
     115
```

<210> SEQ ID NO 81
<211> LENGTH: 115
<212> TYPE: PRT
<213> ORGANISM: Artificial sequence
<220> FEATURE:
<223> OTHER INFORMATION: VH H1028

<400> SEQUENCE: 81

```
              1               5                  10                 15
Glu Val Gln Leu Val Gln Ser Gly Gly Gly Leu Val Gln Pro Gly Gly

Ser Leu Arg Leu Ser Cys Ala Ala Ser Gly Phe Thr Phe Ser Arg Asn
              20                 25                 30

Ala Met Phe Trp Val Arg Gln Ala Pro Gly Lys Gly Leu Glu Trp Val
              35                 40                 45

Ser Gly Ile Gly Thr Gly Gly Ala Thr Ser Tyr Ala Asp Ser Val Lys
              50                 55                 60

Gly Arg Phe Thr Ile Ser Arg Asp Asn Ala Lys Asn Ser Leu Tyr Leu
 65               70                 75                 80

Gln Met Asn Ser Leu Arg Ala Glu Asp Thr Ala Val Tyr Tyr Cys Ala
              85                 90                 95

Arg Gly Arg Tyr Tyr Phe Pro Trp Trp Gly Gln Gly Thr Leu Val Thr
              100                105                110

Val Ser Ser
     115
```

<210> SEQ ID NO 82
<211> LENGTH: 115
<212> TYPE: PRT
<213> ORGANISM: Artificial sequence
<220> FEATURE:
<223> OTHER INFORMATION: VH H1027

<400> SEQUENCE: 82

```
              1               5                  10                 15
Glu Val Gln Leu Val Glu Ser Gly Gly Gly Leu Val His Pro Gly Gly

Ser Leu Arg Leu Ser Cys Ala Ala Ser Gly Phe Thr Phe Ser Arg Asn
              20                 25                 30

Ala Met Phe Trp Val Arg Gln Ala Pro Gly Lys Gly Leu Glu Trp Val
              35                 40                 45

Ser Gly Ile Gly Thr Gly Gly Ala Thr Ser Tyr Ala Asp Ser Val Lys
              50                 55                 60
```

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115

<210> SEQ ID NO 83
<211> LENGTH: 115
<212> TYPE: PRT
<213> ORGANISM: Artificial sequence
<220> FEATURE:
<223> OTHER INFORMATION: VH H1026

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115

<210> SEQ ID NO 84
<211> LENGTH: 115
<212> TYPE: PRT
<213> ORGANISM: Artificial sequence
<220> FEATURE:
<223> OTHER INFORMATION: VH H1030

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115

```
<210> SEQ ID NO 85
<211> LENGTH: 115
<212> TYPE: PRT
<213> ORGANISM: Artificial sequence
<220> FEATURE:
<223> OTHER INFORMATION: VH H1029

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115

<210> SEQ ID NO 86
<211> LENGTH: 115
<212> TYPE: PRT
<213> ORGANISM: Artificial sequence
<220> FEATURE:
<223> OTHER INFORMATION: VH H1025

<400> SEQUENCE: 86

Glu Val Gln Leu Val Gln Ser Gly Gly Gly Leu Val His Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115

<210> SEQ ID NO 87
<211> LENGTH: 115
<212> TYPE: PRT
<213> ORGANISM: Artificial sequence
<220> FEATURE:
<223> OTHER INFORMATION: VH H1024

<400> SEQUENCE: 87
```

-continued

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
            85                  90                  95

Arg Gly Arg Tyr Tyr Phe Pro Trp Trp Gly Gln Gly Thr Leu Val Thr
            100                 105                 110

Val Ser Ser
        115

<210> SEQ ID NO 88
<211> LENGTH: 115
<212> TYPE: PRT
<213> ORGANISM: Artificial sequence
<220> FEATURE:
<223> OTHER INFORMATION: VH H1023

<400> SEQUENCE: 88

Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
            85                  90                  95

Arg Gly Arg Tyr Tyr Phe Pro Trp Trp Gly Gln Gly Thr Leu Val Thr
            100                 105                 110

Val Ser Ser
        115

<210> SEQ ID NO 89
<211> LENGTH: 115
<212> TYPE: PRT
<213> ORGANISM: Artificial sequence
<220> FEATURE:
<223> OTHER INFORMATION: VH H1022

<400> SEQUENCE: 89

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

```
Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115

<210> SEQ ID NO 90
<211> LENGTH: 115
<212> TYPE: PRT
<213> ORGANISM: Artificial sequence
<220> FEATURE:
<223> OTHER INFORMATION: VH H1032

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115

<210> SEQ ID NO 91
<211> LENGTH: 115
<212> TYPE: PRT
<213> ORGANISM: Artificial sequence
<220> FEATURE:
<223> OTHER INFORMATION: VH H1031

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
```

<210> SEQ ID NO 92
<211> LENGTH: 115
<212> TYPE: PRT
<213> ORGANISM: Artificial sequence
<220> FEATURE:
<223> OTHER INFORMATION: VH H1000

<400> SEQUENCE: 92

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115

<210> SEQ ID NO 93
<211> LENGTH: 115
<212> TYPE: PRT
<213> ORGANISM: Artificial sequence
<220> FEATURE:
<223> OTHER INFORMATION: VH H1001

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115

<210> SEQ ID NO 94
<211> LENGTH: 209
<212> TYPE: PRT
<213> ORGANISM: human
<220> FEATURE:
<223> OTHER INFORMATION: sIL4Ralpha

<400> SEQUENCE: 94

```
Gly Asn Met Lys Val Leu Gln Glu Pro Thr Cys Val Ser Asp Tyr Met
1               5                   10                  15

Ser Ile Ser Thr Cys Glu Trp Lys Met Asn Gly Pro Thr Asn Cys Ser
            20                  25                  30

Thr Glu Leu Arg Leu Leu Tyr Gln Leu Val Phe Leu Leu Ser Glu Ala
        35                  40                  45

His Thr Cys Ile Pro Glu Asn Asn Gly Gly Ala Gly Cys Val Cys His
    50                  55                  60

Leu Leu Met Asp Asp Val Val Ser Ala Asp Asn Tyr Thr Leu Asp Leu
65                  70                  75                  80

Trp Ala Gly Gln Gln Leu Leu Trp Lys Gly Ser Phe Lys Pro Ser Glu
            85                  90                  95

His Val Lys Pro Arg Ala Pro Gly Asn Leu Thr Val His Thr Asn Val
            100                 105                 110

Ser Asp Thr Leu Leu Leu Thr Trp Ser Asn Pro Tyr Pro Pro Asp Asn
        115                 120                 125

Tyr Leu Tyr Asn His Leu Thr Tyr Ala Val Asn Ile Trp Ser Glu Asn
        130                 135                 140

Asp Pro Ala Asp Phe Arg Ile Tyr Asn Val Thr Tyr Leu Glu Pro Ser
145                 150                 155                 160

Leu Arg Ile Ala Ala Ser Thr Leu Lys Ser Gly Ile Ser Tyr Arg Ala
                165                 170                 175

Arg Val Arg Ala Trp Ala Gln Cys Tyr Asn Thr Thr Trp Ser Glu Trp
                180                 185                 190

Ser Pro Ser Thr Lys Trp His Asn Ser Tyr Arg Glu Pro Phe Glu Gln
        195                 200                 205

His
```